(12) United States Patent
Truckai et al.

(10) Patent No.: US 7,169,146 B2
(45) Date of Patent: Jan. 30, 2007

(54) ELECTROSURGICAL PROBE AND METHOD OF USE

(75) Inventors: Csaba Truckai, Saratoga, CA (US); John H. Shadduck, Tiburon, CA (US)

(73) Assignee: SurgRx, Inc., Redwood City, CA (US)

( * ) Notice: Subject to any disclaimer, the term of this patent is extended or adjusted under 35 U.S.C. 154(b) by 430 days.

(21) Appl. No.: 10/781,925

(22) Filed: Feb. 17, 2004

(65) Prior Publication Data

US 2004/0199161 A1   Oct. 7, 2004

Related U.S. Application Data

(60) Provisional application No. 60/447,535, filed on Feb. 14, 2003.

(51) Int. Cl.
*A61B 18/18* (2006.01)
(52) U.S. Cl. .............. 606/41; 606/49; 606/50; 606/51; 606/52
(58) Field of Classification Search .......... 606/41, 606/49–52
See application file for complete search history.

(56) References Cited

U.S. PATENT DOCUMENTS

| | | | |
|---|---|---|---|
| 659,409 | A | 10/1900 | Mosher |
| 1,586,645 | A | 6/1926 | Bierman |
| 1,798,902 | A | 3/1931 | Raney |
| 1,881,250 | A | 10/1932 | Tomlinson |
| 2,031,682 | A | 2/1936 | Wappler et al. |
| 3,651,811 | A | 3/1972 | Hildebrandt et al. |
| 3,685,518 | A | 8/1972 | Beuerle et al. |
| 3,730,188 | A | 5/1973 | Ellman |

(Continued)

FOREIGN PATENT DOCUMENTS

EP   341 446 A2   4/1989

(Continued)

OTHER PUBLICATIONS

Corson, S.L., "Two new laparoscopic instruments: Bipolar sterilizing forceps and uterine manipulator," *Medical Instrumetation*, 11(1): 7-8 (1977).

(Continued)

*Primary Examiner*—Michael Peffley
*Assistant Examiner*—Alex Toy
(74) *Attorney, Agent, or Firm*—Townsend and Townsend and Crew LLP

(57) ABSTRACT

An electrosurgical instrument that allows precise modulation of active Rf density in an engaged tissue volume. The working end of the instrument has a tissue-contacting surface of a conductive-resistive matrix that is variably resistive depending on its temperature. The matrix comprises a positive temperature coefficient (PTC) polymeric material hat exhibits very large increases in resistivity as any local portion increases beyond a selected temperature. In a method of use, the polymeric PTC material senses the temperature of engaged tissue in a manner akin to pixel-by-pixel sensing and thereby changes its resistance in a corresponding pixel-by-pixel manner. The instrument further carries cooling means to cause accelerated thermal relaxation of the PTC matrix during use to make the engagement surface highly responsive to temperature changes that in turn alter the matrix between being electrically conductive and electrically resistive.

50 Claims, 23 Drawing Sheets

U.S. PATENT DOCUMENTS

| | | | |
|---|---|---|---|
| 3,768,482 A | 10/1973 | Shaw | |
| 3,826,263 A | 7/1974 | Cage et al. | |
| 4,092,986 A | 6/1978 | Schneiderman | |
| 4,198,957 A | 4/1980 | Cage et al. | |
| 4,219,025 A | 8/1980 | Johnson | |
| 4,231,371 A | 11/1980 | Lipp | |
| 4,232,676 A | 11/1980 | Herczog | |
| 4,271,838 A | 6/1981 | Lasner et al. | |
| 4,353,371 A | 10/1982 | Cosman | |
| 4,370,980 A | 2/1983 | Lottick | |
| 4,375,218 A | 3/1983 | DiGeronimo | |
| 4,492,231 A | 1/1985 | Auth | |
| 4,590,934 A | 5/1986 | Malis et al. | |
| 4,608,981 A | 9/1986 | Rothfuss et al. | |
| 4,633,874 A | 1/1987 | Chow et al. | |
| 4,655,216 A | 4/1987 | Tischer | |
| 4,671,274 A | 6/1987 | Sorochenko | |
| 4,691,703 A | 9/1987 | Auth et al. | |
| 4,763,669 A | 8/1988 | Jaeger | |
| 4,785,807 A | 11/1988 | Blanch | |
| 4,848,337 A | 7/1989 | Shaw et al. | |
| 4,850,353 A | 7/1989 | Stasz et al. | |
| 4,887,612 A | 12/1989 | Esser et al. | |
| 4,940,468 A | 7/1990 | Petillo | |
| 4,958,539 A | 9/1990 | Stasz et al. | |
| 4,969,885 A | 11/1990 | Farin | |
| 4,985,030 A | 1/1991 | Melzer et al. | |
| 5,009,656 A | 4/1991 | Reimels | |
| 5,057,106 A | 10/1991 | Kasevich et al. | |
| 5,057,107 A | 10/1991 | Parins et al. | |
| 5,085,659 A | 2/1992 | Rydell | |
| 5,104,025 A | 4/1992 | Main et al. | |
| 5,122,137 A | 6/1992 | Lennox | |
| 5,147,356 A | 9/1992 | Bhatta | |
| 5,147,357 A | 9/1992 | Rose et al. | |
| 5,151,102 A | 9/1992 | Kamiyama et al. | |
| 5,190,541 A | 3/1993 | Abele et al. | |
| 5,201,900 A | 4/1993 | Nardella | |
| 5,207,691 A | 5/1993 | Nardella | |
| 5,258,006 A | 11/1993 | Rydell et al. | |
| 5,267,998 A | 12/1993 | Hagen | |
| 5,269,780 A | 12/1993 | Roos | |
| 5,290,286 A | 3/1994 | Parins | |
| 5,306,280 A | 4/1994 | Bregen et al. | |
| 5,308,311 A | 5/1994 | Eggers et al. | |
| 5,324,289 A | 6/1994 | Eggers | |
| 5,336,221 A | 8/1994 | Anderson | |
| 5,360,428 A | 11/1994 | Hutchinson, Jr. | |
| 5,364,389 A | 11/1994 | Anderson | |
| 5,389,098 A | 2/1995 | Tsuruta et al. | |
| 5,403,312 A | 4/1995 | Yates et al. | |
| 5,417,687 A | 5/1995 | Nardella et al. | |
| 5,443,463 A | 8/1995 | Stern et al. | |
| 5,445,638 A | 8/1995 | Rydell et al. | |
| 5,451,224 A | 9/1995 | Goble et al. | |
| 5,458,598 A | 10/1995 | Feinberg et al. | |
| 5,480,397 A | 1/1996 | Eggers et al. | |
| 5,480,398 A | 1/1996 | Eggers | |
| 5,507,106 A | 4/1996 | Fox | |
| 5,531,744 A | 7/1996 | Nardella et al. | |
| 5,571,153 A | 11/1996 | Wallsten | |
| 5,573,535 A | 11/1996 | Viklund | |
| 5,593,406 A | 1/1997 | Eggers et al. | |
| 5,611,798 A | 3/1997 | Eggers | |
| 5,624,452 A | 4/1997 | Yates | |
| 5,674,220 A | 10/1997 | Fox et al. | |
| 5,693,051 A | 12/1997 | Schulze et al. | |
| 5,716,366 A | 2/1998 | Yates | |
| 5,735,848 A | 4/1998 | Yates et al. | |
| 5,755,717 A | 5/1998 | Yates et al. | |
| 5,766,166 A | 6/1998 | Hooven | |
| 5,776,130 A | 7/1998 | Buysse et al. | |
| 5,797,938 A | 8/1998 | Paraschal et al. | |
| 5,800,449 A | 9/1998 | Wales | |
| 5,807,392 A | 9/1998 | Eggers | |
| 5,833,690 A | 11/1998 | Yates et al. | |
| 5,911,719 A | 6/1999 | Eggers | |
| 5,947,984 A | 9/1999 | Whipple | |
| 6,019,758 A | 2/2000 | Slater | |
| 6,039,733 A | 3/2000 | Buysse et al. | |
| 6,074,389 A | 6/2000 | Levine et al. | |
| 6,086,586 A | 7/2000 | Hooven | |
| 6,113,598 A | 9/2000 | Baker | |
| 6,139,508 A | 10/2000 | Simpson et al. | |
| 6,152,923 A | 11/2000 | Ryan | |
| 6,162,220 A | 12/2000 | Nezhat | |
| 6,174,309 B1 | 1/2001 | Wrublewski et al. | |
| 6,176,857 B1 | 1/2001 | Ashley | |
| 6,179,834 B1 | 1/2001 | Buysse et al. | |
| 6,179,835 B1 | 1/2001 | Panescu et al. | |
| 6,179,837 B1 | 1/2001 | Hooven | |
| 6,187,003 B1 | 2/2001 | Buysse et al. | |
| 6,190,386 B1 | 2/2001 | Rydell | |
| 6,193,709 B1 | 2/2001 | Miyawaki et al. | |
| 6,270,497 B1 | 8/2001 | Sekino et al. | |
| 6,273,887 B1 | 8/2001 | Yamauchi et al. | |
| 6,277,117 B1 | 8/2001 | Tetzlaff et al. | |
| 6,296,640 B1 | 10/2001 | Wampler et al. | |
| 6,328,703 B1 | 12/2001 | Murakami | |
| 6,334,861 B1 | 1/2002 | Chandler et al. | |
| 6,350,264 B1 | 2/2002 | Hooven | |
| 6,352,536 B1 | 3/2002 | Buysse et al. | |
| 6,398,779 B1 | 6/2002 | Buysse et al. | |
| 6,409,725 B1 | 6/2002 | Khandkar et al. | |
| 6,451,018 B1 | 9/2002 | Lands et al. | |
| 6,458,128 B1 | 10/2002 | Schulze | |
| 6,458,130 B1 | 10/2002 | Frazier et al. | |
| 6,464,704 B1 | 10/2002 | Schmaltz et al. | |
| 6,468,275 B1 | 10/2002 | Wampler et al. | |
| 6,500,176 B1 | 12/2002 | Truckai et al. | |
| 6,511,480 B1 | 1/2003 | Tetzlaff et al. | |
| 6,527,767 B1 | 3/2003 | Wang et al. | |
| 6,533,784 B1 | 3/2003 | Truckai et al. | |
| 6,554,829 B1 | 4/2003 | Schulze et al. | |
| 6,575,968 B1 | 6/2003 | Eggers et al. | |
| 6,585,735 B1 | 7/2003 | Frazier et al. | |
| 6,632,193 B1 | 10/2003 | Davison et al. | |
| 6,652,521 B1 | 11/2003 | Schulze | |
| 2002/0052599 A1 | 5/2002 | Goble | |
| 2002/0115997 A1 | 8/2002 | Truckai et al. | |
| 2002/0120266 A1 | 8/2002 | Truckai et al. | |
| 2002/0169392 A1 | 11/2002 | Truckai et al. | |
| 2002/0177848 A1 | 11/2002 | Truckai et al. | |
| 2003/0018327 A1 | 1/2003 | Truckai et al. | |
| 2003/0050635 A1 | 3/2003 | Truckai et al. | |
| 2003/0055417 A1 | 3/2003 | Truckai et al. | |
| 2003/0069579 A1 | 4/2003 | Truckai et al. | |
| 2003/0078573 A1 | 4/2003 | Truckai et al. | |
| 2003/0078577 A1 | 4/2003 | Truckai et al. | |
| 2003/0078578 A1 | 4/2003 | Truckai et al. | |
| 2003/0114851 A1 | 6/2003 | Truckai et al. | |
| 2003/0125727 A1 | 7/2003 | Truckai et al. | |
| 2003/0139741 A1 | 7/2003 | Goble et al. | |
| 2003/0144652 A1 | 7/2003 | Baker et al. | |

FOREIGN PATENT DOCUMENTS

| | | |
|---|---|---|
| EP | 517 244 B1 | 3/1996 |
| EP | 518 230 B1 | 5/1996 |

| FR | 2536924 A1 | 6/1984 |
| FR | 2647683 A1 | 12/1990 |
| GB | 2037167 A | 7/1980 |
| GB | 2066104 A | 7/1981 |
| GB | 2133290 A | 7/1984 |
| GB | 2161082 A | 1/1986 |
| SU | 575103 | 10/1977 |
| WO | WO 93/08754 A1 | 5/1993 |
| WO | WO 94/24949 A1 | 11/1994 |
| WO | WO 94/24951 A1 | 11/1994 |

OTHER PUBLICATIONS

Burton, J.D.K., "New Inventions," *The Lancet*, pp. 650-651 (1959).

Naradella, P.C., "Radio Frequency Energy and Impedance Feedback," *Proc. SPIE, Catheter-Based Sensing and Imaging Technology*, 1068: 42-48 (1989).

Vallfors et al., "Automatically controlled bipolar electrocoagulation—'COA-COMP'," *Neurosurg Rev.*, 187-190 (1984).

ELECTROSURGICAL PROBE AND METHOD OF USE

CROSS-REFERENCES TO RELATED APPLICATIONS

This application claims benefit of Provisional U.S. Patent Application Ser. No. 60/447,535 filed Feb. 14, 2003 entitled "Electrosurgical Probe and Method."

BACKGROUND OF THE INVENTION

1. Field of the Invention

This invention relates to medical devices and methods and more particularly relates to electrosurgical jaw, probe and needle structures with at least one polymer positive temperature coefficient of resistance (PTC) body portion for sensing tissue temperature and modulating ohmic tissue heating together with multiple circuitry components for intraoperative control of voltage applied to the engaged tissue.

2. Description of the Related Art

In the prior art, various energy sources such as radiofrequency (RF) sources, ultrasound sources and lasers have been developed to coagulate, seal or join together tissues volumes in open and laparoscopic surgeries. The most important surgical application relates to sealing blood vessels which contain considerable fluid pressure therein. In general, no instrument working ends using any energy source have proven reliable in creating a "tissue weld" or "tissue fusion" that has very high strength immediately post-treatment. For this reason, the commercially available instruments, typically powered by RF or ultrasound, are mostly limited to use in sealing small blood vessels and tissues masses with microvasculature therein. The prior art RF devices also fail to provide seals with substantial strength in anatomic structures having walls with irregular or thick fibrous content, in bundles of disparate anatomic structures, in substantially thick anatomic structures, or in tissues with thick fascia layers (e.g., large diameter blood vessels).

In a basic bi-polar RF jaw arrangement, each face of opposing first and second jaws comprises an electrode and RF current flows across the captured tissue between the opposing polarity electrodes. Such prior art RF jaws that engage opposing sides of tissue typically cannot cause uniform thermal effects in the tissue—whether the captured tissue is thin or substantially thick. As RF energy density in tissue increases, the tissue surface becomes desiccated and resistant to additional ohmic heating. Localized tissue desiccation and charring can occur almost instantly as tissue impedance rises, which then can result in a non-uniform seal in the tissue. The typical prior art RF jaws can cause further undesirable effects by propagating RF density laterally from the engaged tissue thus causing unwanted collateral thermal damage.

The commercially available RF sealing instruments typically adopt a "power adjustment" approach to attempt to control RF flux in tissue wherein a system controller rapidly adjusts the level of total power delivered to the jaws' electrodes in response to feedback circuitry coupled to the electrodes that measures tissue impedance or electrode temperature. Another approach used in the prior art consists of jaws designs that provide spaced apart of offset electrodes wherein the opposing polarity electrode portion s are spaced apart by an insulator material—which may cause current to flow within an extended path through captured tissue rather that simply between opposing electrode surfaces of the first and second jaws. Electrosurgical grasping instruments having jaws with electrically-isolated electrode arrangements in cooperating jaws faces were proposed by Yates et al. in U.S. Pat. Nos. 5,403,312; 5,735,848; and 5,833,690. In general, the prior art instruments cannot reliably create high strength seals in larger arteries and veins.

BRIEF SUMMARY OF THE INVENTION

The electrosurgical instrument corresponding to the invention provides novel means for modulating RF energy application to biological tissue to create high strength thermally welds or seals in targeted tissues. The system allows for a "one-step" welding-transecting procedure wherein the surgeon can contemporaneously (i) engage tissue within a jaw structure (ii) apply RF energy to the tissue, and (iii) transect the tissue. Such one-step welding and transecting has never been considered in the prior art.

Another particular objective is to provide a jaw structure that can engage and weld tissue bundles, defined herein as bundles of disparate tissue types (e.g., fat, blood vessels, fascia, etc.). For the welding of tissue bundles, the jaw surfaces must apply differential energy levels to each different tissue type simultaneously that has not been accomplished in the prior art. The invention provides an electrosurgical system that applies differential energy levels across the jaws engagement surfaces with "smart" materials without the need for complex feedback circuitry coupled to thermocouples or other sensors in the jaw structure.

In order to create the most effective "weld" in tissue, the targeted volume of tissue must be uniformly elevated to the temperature needed to denature proteins therein. To create a "weld" in tissue, collagen, elastin and other protein molecules within an engaged tissue volume must be denatured by breaking the inter- and intra-molecular hydrogen bonds—followed by re-crosslinking on thermal relaxation to create a fused-together tissue mass. It can be easily understood that ohmic heating in tissue—if not uniform—an at best create localized spots of truly "welded" tissue. Such a non-uniformly denatured tissue volume still is "coagulated" and will prevent blood flow in small vasculature that contains little pressure. However, such non-uniformly denatured tissue will not create a seal with significant strength, for example in 2 mm. to 10 mm. arteries that contain high pressures.

The systems and methods corresponding to invention relate to creating thermal "welds" or "fusion" within native tissue volumes. The alternative terms of tissue "welding" and tissue "fusion" are used interchangeably herein to describe thermal treatments of a targeted tissue volume that result in a substantially uniform fused-together tissue mass, for example in welding blood vessels that exhibit substantial burst strength immediately post-treatment. The strength of such welds is particularly important (i) for permanently sealing blood vessels in vessel transection procedures, (ii) for welding organ margins in resection procedures, (iii) for welding other anatomic ducts wherein permanent closure is required, and also (iv) for vessel anastamosis, vessel closure or other procedures that join together anatomic structures or portions thereof. The welding or fusion of tissue as disclosed herein is to be distinguished from "coagulation", "sealing", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the affected tissue.

At the molecular level, the phenomena of truly "welding" tissue as disclosed herein may not be fully understood. However, the authors have identified the parameters at which tissue welding can be accomplished. An effective "weld" as disclosed herein results from the thermally-induced denaturation of collagen, elastin and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in "protein entanglement" as re-crosslinking or renaturation occurs to thereby cause a uniform fused-together mass.

In general, the electrosurgical jaw structure corresponding to the invention comprises first and second opposing jaws that carry variable impedance bodies for modulating RF energy delivery to engaged tissue.

The electrosurgical jaws advantageously use first and second energy-delivery jaw surfaces coupled in series to an RF source that utilize first and second variable impedance or positive temperature coefficient (PTC) bodies in the jaw surfaces for controlling electrosurgical energy parameters such as voltage and current within engaged tissue.

The electrosurgical jaws advantageously use first and second 3D variable impedance bodies that define different temperature-impedance curves for controlling ohmic heating of tissue.

In another aspect of the invention, an active cooling system is provided to cool the PTC material during use to cause the PTC material to change rapidly between conductive and resistive states. In one embodiment, an electrosurgical instrument comprises a working end having a surface layer at an exterior portion of the working end, the surface layer comprising a matrix of polymeric PTC composition adapted to deliver electrical current to tissue, and a cooling structure at an interior portion of the working end, wherein the cooling structure cools the PTC matrix to lower the temperature of one or more portions of the PTC matrix.

In many embodiments, the thickness of the surface layer is selected to vary the energy-modulating properties of the working end. Generally, the surface layer has a thickness of less than about 500 microns, typically within about 0.1 microns and 200 microns, and preferably between about 0.5 microns and 100 microns.

In one embodiment of the invention, the cooling structure passively cools the PTC matrix. The cooling structure may comprise a thermally conductive material forming an electrode which conducts electrical current from a power source to the PTC matrix. Preferably, the cross-section of the conductive material is significantly larger than the PTC surface layer. In some cases, the conductive material has a recess to accelerate cooling of the conductive portion. Generally, the cooling structure may comprise any thermally and electrically conductive material, such as a copper-beryllium alloy, copper, aluminum, silver, or gold.

In another embodiment, the cooling structure actively cools the PTC matrix. A typical cooling structure may communicate with a fluid-cooling circulation system and comprise a thermally conductive material forming an electrode which conducts electrical current from a power source to the PTC matrix. In some cases, the fluid-cooling system may be connected to a fluid source, wherein the conductive portion has a flow channel to form a flow loop through which the fluid source circulates a fluid. The system may further comprise a heat exchanger, wherein the fluid pump circulates the fluid through the heat exchanger. The fluid comprise a liquid such as water, or a cooling gas comprising a cryogen such as freon or $CO_2$.

In embodiments using a cooling gas, the system may further comprise an expansion chamber, wherein the cooling gas absorbs heat as it changes its phase state while in the expansion chamber. Generally, an inflow channel and outflow channel are provided for circulating the gas between the fluid pump and the expansion chamber. In an alternative embodiment, the cooling structure may comprise a Peltier element.

In either the passive or active cooling embodiments, the surface layer generally defines an engagement surface for engaging tissue. In one aspect of the invention, the engagement surface is carried on the working end of a probe. Alternatively, the engagement surface may be carried on the working end of a jaw structure, wherein the jaw structure comprises paired first and second jaws moveable between an open position and a closed position. Typically, at least one jaw defines an engagement plane, the engagement plane carrying at least a portion of the engagement surface. A plurality of electrodes may be formed on the jaw structure so that power may be delivered to the electrodes in a bipolar configuration.

In another aspect of the invention, a method is disclosed for the controlled delivery of energy to tissue. The method comprises the step of engaging tissue with an engagement surface at least a portion of which comprises a body of temperature-responsive variable impedance material that is intermediate opposing polarity conductor regions operatively coupled to an RF power source. Current flow is then delivered to the engaged tissue and engagement surface to cause ohmic heating of the tissue, wherein the ohmically heated tissue conductively heats adjacent regions of the engagement surface, and wherein the engagement surface varies its impedance to modulate current flow within the tissue and engagement surface. Contemporaneously, the engagement surface is cooled to cause faster modulation of the temperature of one or more portions of the variable impedance material during energy application. In other words, the body of variable impedance material defines a switching range at which the electrical resistance substantially increases in a selected temperature range to terminate current flow at least a portion of the variable impedance body that is within the switching range, wherein cooling the engagement surface accelerates the temperature response of the variable impedance body and localized the switching effect at the engagement surface.

In some embodiments, cooling the engagement surface comprises passively cooling the engagement surface. Cooling the engagement surface may be done by providing a cooling structure at an interior of the working end, wherein the cooling structure comprises a thermally conductive material. Alternatively, cooling the engagement surface comprises actively cooling the engagement surface. In such embodiments, fluid-cooling circulation system is employed to circulate a fluid through a flow channel proximal to the engagement surface.

In yet another aspect of the invention, an electrosurgical instrument comprises an introducer member having at least one working surface for engaging tissue, wherein at least a portion of the at least one working surface comprises a polymeric PTC composition, and a conductor at an interior of the PTC composition, the conductor having at least one open region at an interior of the conductor for cooling the PTC composition. As with the above embodiments, the conductor comprises an electrically conductive material forming an electrode, the electrode connected to a radiofrequency power source to ohmically heat the tissue. The conductive material may also be thermally conductive to act as a heat sink. Typically, the open region communicates with a fluid-cooling circulation device having a fluid source for providing fluid flow through the at least one open region.

Additional objects and advantages of the invention will be apparent from the following description, the accompanying drawings and the appended claims, wherein like reference numerals are used to refer to like components throughout the drawings.

DETAILED DESCRIPTION OF THE INVENTION

Electrosurgical jaw structure with variable impedance matrices. The objectives of the invention are to delivery energy to targeted tissue volumes in a controlled manner to thermally weld or seal targeted tissue. A particular objective is to contemporaneously (i) engage tissue between paired jaws, (ii) deliver energy to the tissue, and (iii) optionally transect the tissue to provide a "one-step" welding-transecting procedure. Such one-step welding and transecting has never been considered in the prior art. Another particular objective is to provide a jaw structure that can engage and weld tissue bundles, defined herein as bundles of disparate tissue types (e.g., fat, blood vessels, fascia, etc.). For the welding of tissue bundles, the jaw surfaces must apply differential energy levels to each different tissue type simultaneously—again never considered in the prior art. Another particular objective is to provide an electrosurgical system that can apply differential energy levels across the jaws engagement surfaces with "smart" materials without the need for complex feedback circuitry coupled to thermocouples or other sensors in the jaw structure. Such energy modulation by smart engagement surface has never been considered in the prior art.

It has been found that very high compression of engaged tissue in combination with controlled RF energy delivery is optimal for welding the engaged tissue volume. Additionally, it has been found that ohmic heating and dehydration of tissue in the process of closing the jaw structure greatly assists in the ultimate compression of tissue (particularly tissue bundles) to the desired thickness of a membrane. With the engaged tissue in membrane thickness in a controlled gap between the engagement surfaces of the jaw structure, e.g., from about 0.001" to about 0.05", the method for controlling ohmic heating in tissue can be optimized (as described below).

Figure 1:
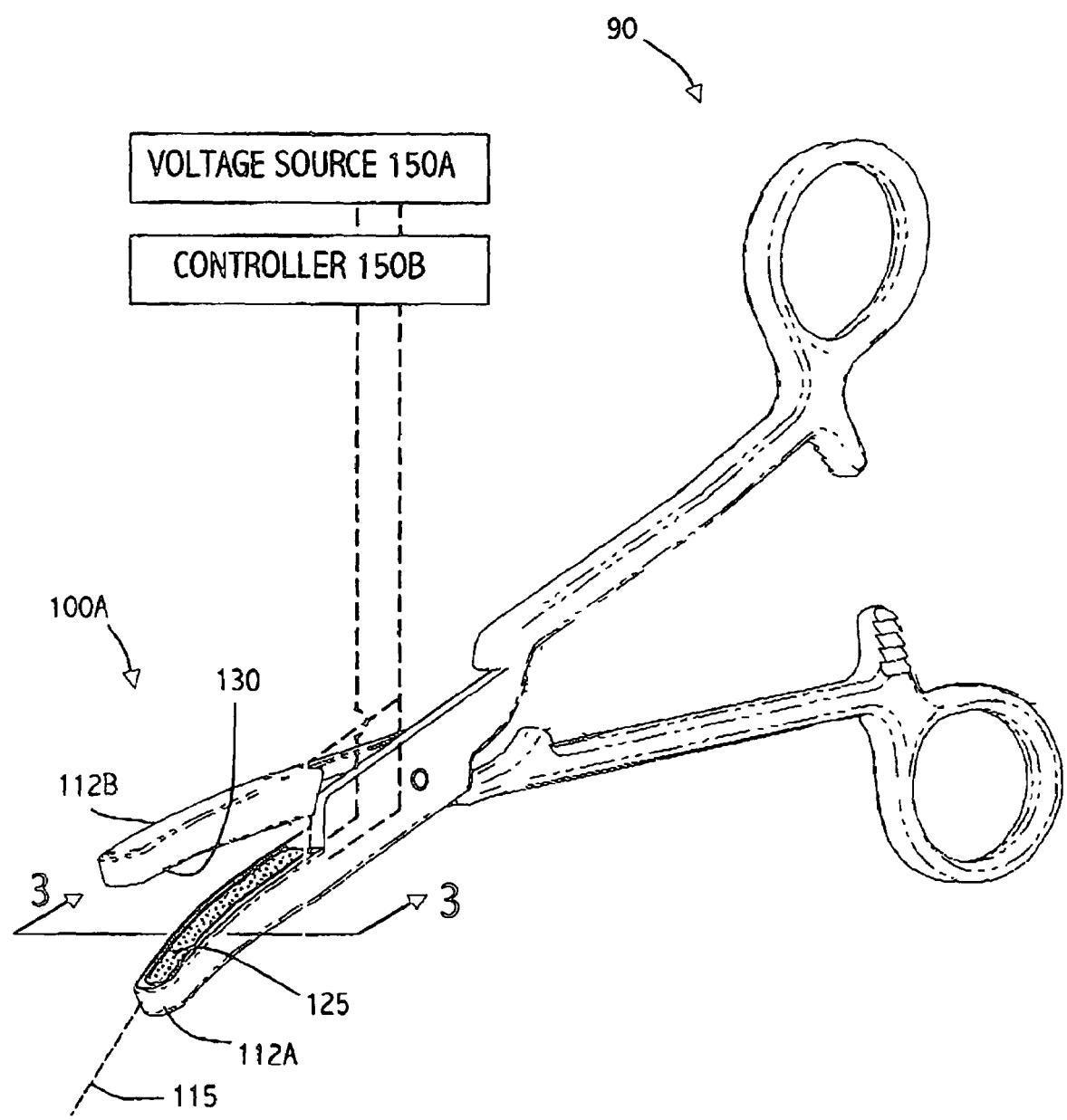
FIG. 1 is a perspective view of an exemplary surgical instrument with and a jaw structure carrying variable impedance matrix bodies for tissue welding corresponding to the invention, the matrix bodies coupled to an RF source via series and parallel circuits for modulating ohmic heating in engaged tissue.

FIG. 1 illustrates an exemplary forceps-type instrument 90 with a working end or electrosurgical jaw structure 100A corresponding to the invention that comprises first (lower) jaw element 112A and second (upper) jaw element 112B that close or approximate about axis 115 that is straight or curved. It should be appreciated that the jaw elements can be of any curved or straight shape for open or endoscopic surgeries with a scissors-type actions or with one or more cam mechanism as is known in the art. The jaws also can carry a sliding cutting blade as will be described below.

Figure 2:
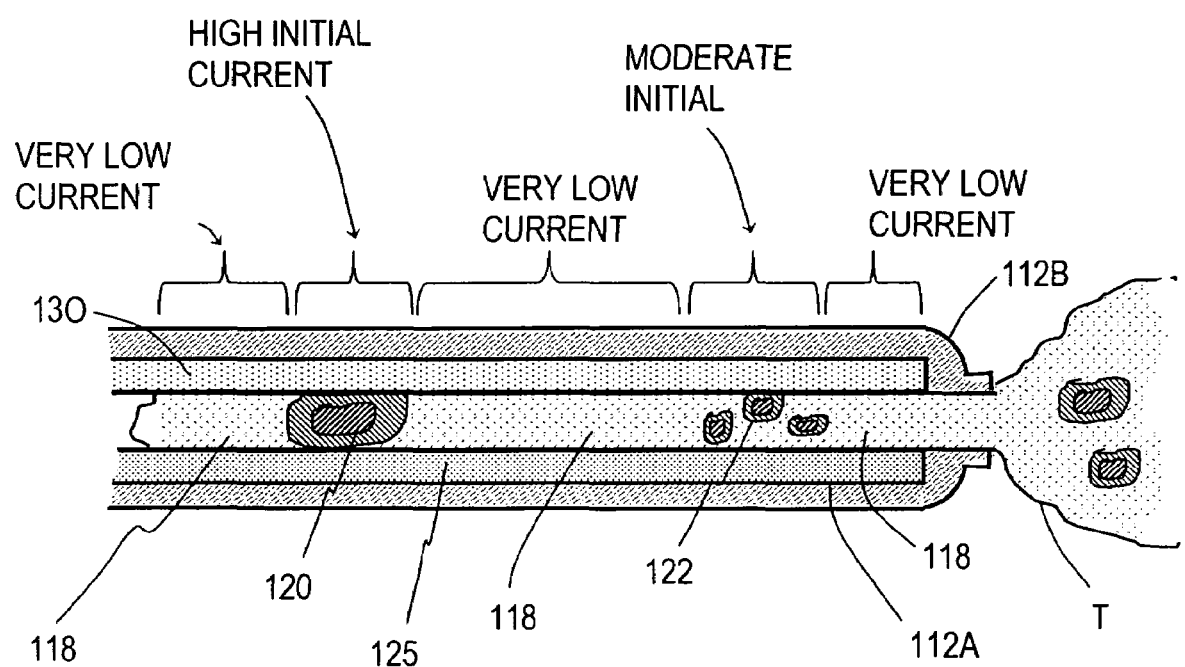
FIG. 2 is a graphic representation of opposing jaws engaging a tissue bundle comprising large blood vessels, fatty tissue and small blood vessels embedded in the fat.

Now turning to the electrosurgical functionality of the invention, FIG. 2 graphically illustrates one of the objectives of the invention. In FIG. 2, the opposing jaws 112A and 112B are depicted schematically as engaging a tissue bundle T of differentiated tissue types—which is a common occurrence in open and endoscopic surgeries. FIG. 2 depicts a longitudinal sectional view of jaws 112A and 112B and an engaged tissue bundle T that contains, for example, insulative fat 118, large blood vessels 120 and smaller embedded blood vessels 122. The gap between the jaws is not-to-scale, and in an actual jaw structure the compressed tissue bundle T could be reduced to the thickness of a thin membrane. In an actual procedure, the tissue bundle would also contain fascia, ligamentous tissues and other tissues that would exhibit a wide range of hydration levels, electrolyte levels etc. that would locally alter tissue impedance, compressibility etc. For convenience, only three tissue types with three impedance levels are shown in FIG. 2. As indicated graphically by the microcurrents MC in FIG. 2, the objective is to contemporaneously modulate energy densities across the various types of in the tissue bundle T according to the impedance of each engaged tissue type and region. Further, it is necessary to continuously modulate energy delivery to each tissue type as the region dynamically changes in hydration, impedance and geometry. As energy is delivered, the tissue will shrink as it dehydrates.

Figure 3:
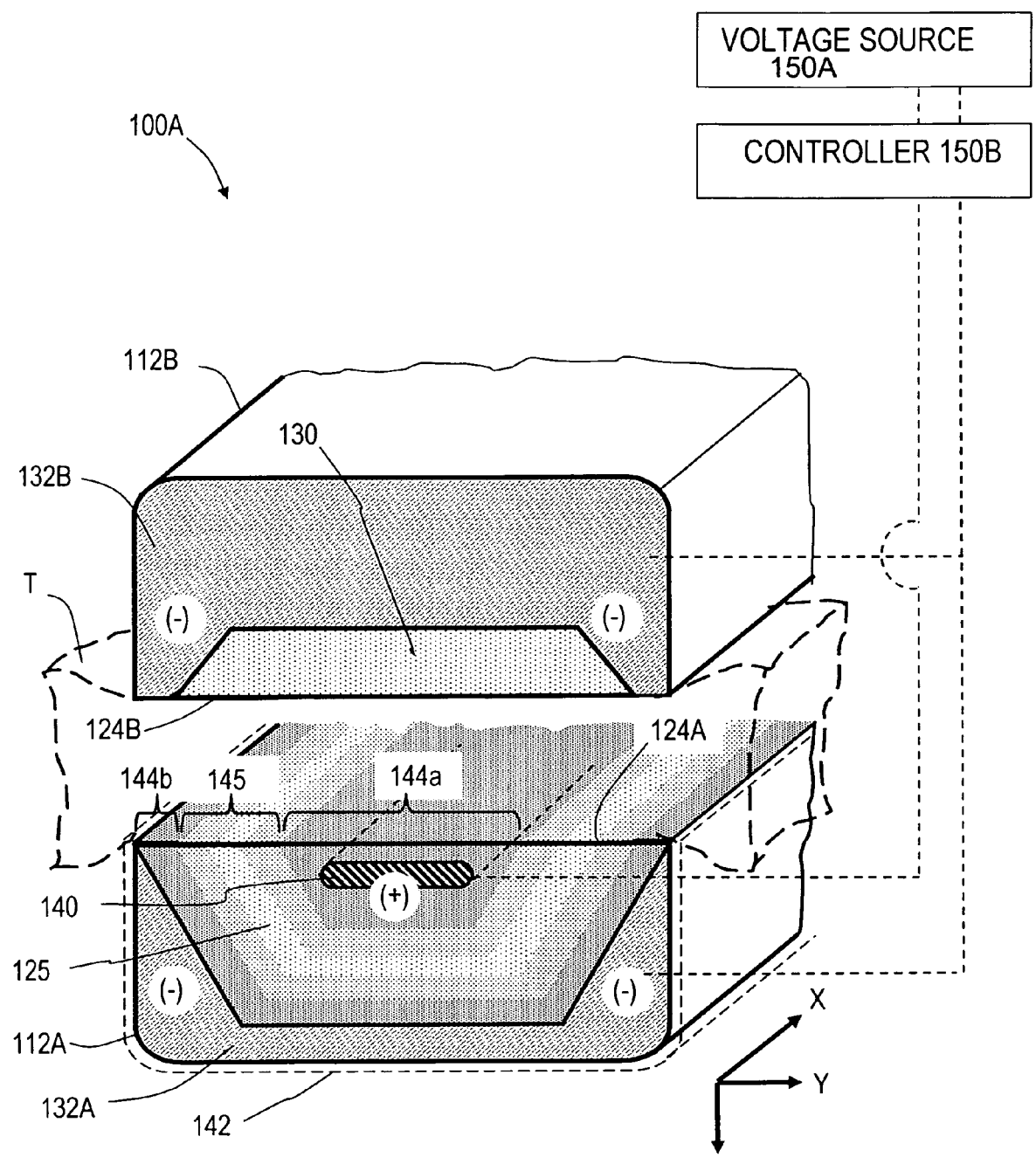
FIG. 3 is a schematic sectional view of the jaw structure of FIG. 1 taken along line 3—3 of FIG. 1 showing the variable impedance matrices in each jaw together with the series and parallel circuits.

FIG. 3 illustrates the tissue-engaging surfaces 124A and 124B of jaws 112A and 112B. Of particular interest, the jaws each carry a three-dimensional (3D) temperature-responsive variable resistive body. The lower jaw 112A carries variable impedance body indicated at 125, also at times referred to herein as a positive temperature coefficient of resistance (PTC) body or matrix. By the term three-dimensional, it is meant for example that variable impedance body 125 defines an axial dimension X and a cross-axial dimension Y about the tissue-engaging surface, as well as defining a substantial depth dimension Z that is orthogonal to the plane of the tissue-engaging surface 124A. In other words the variable resistive body or matrix 125 has a selected thickness dimension in preferred embodiments to provide a multiplicity of varied local current flow paths through the matrix as it dynamically responds to adjacent ohmically heated tissue, as will be described below. The upper jaw 112B in one preferred embodiment as in FIG. 3 carries variable impedance body 130 that again can have any suitable depth dimension.

Still referring to FIG. 3, it can be seen that lower jaw 112A has a structural component or body 132A that is of a suitable electrical conductor material so that it functions as an electrode—that is indicated for convenience with a negative polarity (−). Similarly, the upper jaw 112B has structural component or body 132B that is has the same polarity (−) as the lower jaw body. An electrically conductive member or electrode 140 is provided within variable impedance matrix 125 either at the tissue-engaging surface 124A or proximate the surface as depicted in FIG. 3. Both jaws optionally can have an insulative coating indicated at 142 at the exterior of lower jaw 112A.

In a preferred embodiment as in FIGS. 2 and 3, the variable impedance matrices 125 and 130 in lower jaw 112A and upper jaw 112B comprise a polyethylene or a medical grade silicone polymer that is doped with conductive particles (e.g., carbon). The use of such temperature-responsive variable impedance materials is described for related uses in co-pending U.S. patent applications: Ser. No. 10/351,449 filed Jan. 22, 2003 titled Electrosurgical Instrument and Method of Use; Ser. No. 10/032,867 filed Oct. 22, 2001 titled Electrosurgical Jaw Structure for Controlled Energy Delivery, both of which are incorporated herein by reference. Polymer positive temperature coefficient materials are known in the field of overcurrent protection devices that will trip and become resistive when a selected trip current and temperature is exceeded.

Figure 4A:
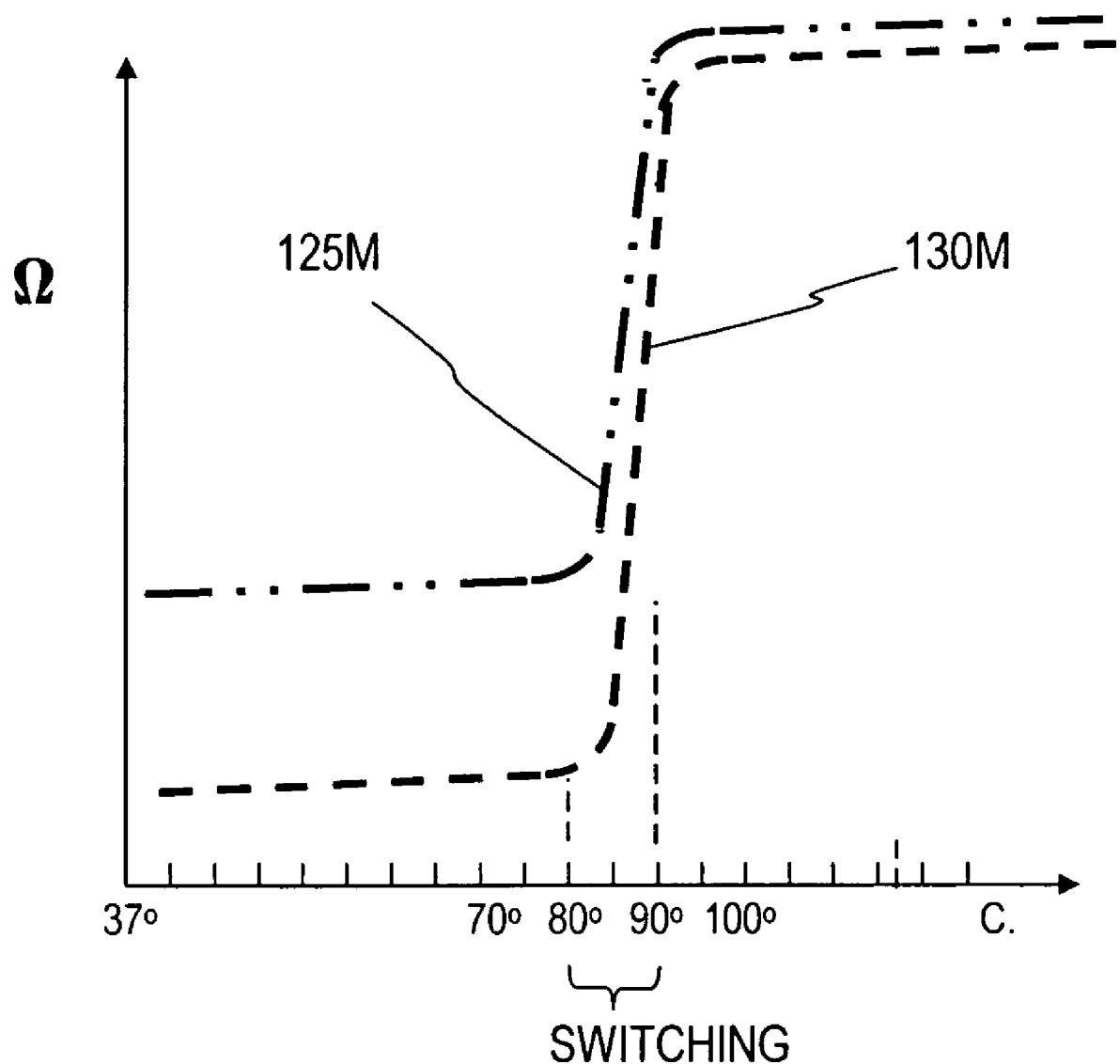
FIG. 4A is a diagram of the temperature-impedance curves of exemplary variable impedance matrix bodies as in FIG. 3.

In general, the temperature-responsive variable impedance materials for use in the invention are fabricated of a non-conductive polymer that exhibits two phases that define greater and lesser conductive states. The first phase is a crystalline or semi-crystalline state where the polymer molecules form long chains and are arranged in a more ordered architecture. When the temperature of the material is elevated, the polymer molecules maintain the crystalline architecture or structure through a selected temperature range. The polymer is designed to transition to an at least partly amorphous phase from the crystalline state at a selected temperature range. In the amorphous state, the molecules are aligned more randomly, and there may be slight changes in material geometry at the macroscale. The non-conductive polymer is combined with a dispersed, highly conductive particles (e.g., carbon micro- or nanoparticles) to form a matrix. In the crystalline phase of the polymer, the carbon particles are packed into the crystalline boundaries and form many conductive paths across and through the matrix material. In this low temperature crystalline state, the polymer-carbon matrix is engineered to have a low resistance. FIG. 4A illustrates the positively-sloped impedance-temperature curve 130M of an exemplary variable impedance matrix 130 of FIG. 3.

For the purposes of the present invention, the jaw structure 100A as in FIG. 3 engages tissue and applies RF energy to the engaged tissue T to cause ohmic heating therein. After the tissue is elevated in temperature, heat is conducted from the engaged tissue T back to the variable impedance matrices 125 and 130 to thereby elevate temperatures in at least surfaces region of the matrices 125 and 130. Details of the actual method of using the matrices to provide high temperature and low temperature process limits are described below. As long as the temperature increase in the matrix portion adjacent the ohmically heated tissue does not cause a phase change in the polymer, current can flow unimpeded through the matrix. When the temperature of the matrix material is elevated to a selected temperature, called a switching range herein, the temperature will cause a phase change in the polymer (see FIG. 4A). The crystalline structure of the polymer will disappear, the polymer volume will expand, and the carbon chains that allow from conduction across the matrix will be broken—an extraordinary increase in resistance. The polymer-carbon matrix can define a resistance measured in milliohms or ohms before the phase change. After the phase change, the matrix' resistance can be measured in megaohms. Current flow can be reduced accordingly or terminated which is used to particular manners to precisely control energy densities in the engaged tissue.

The process described above is reversible so that when a portion of a matrix falls in temperature, the polymer component will return to its crystalline structure and the matrix volume will return its original state. The conductive carbon particles will reform into conductive paths within the interstices of the crystalline polymer architecture. The exact same conductive paths appear not to reform themselves after first use of the matrix, and for this reason the polymer matrices of the invention may be temperature cycled several times in the fabrication process which appears to cause the material to have substantially resettable conductive paths. In the fabrication process, the matrix can also be treated in various processes (e.g., gamma, UV irradiation etc.) to cross-link the polymer or co-polymers of the matrix.

Figure 4B:
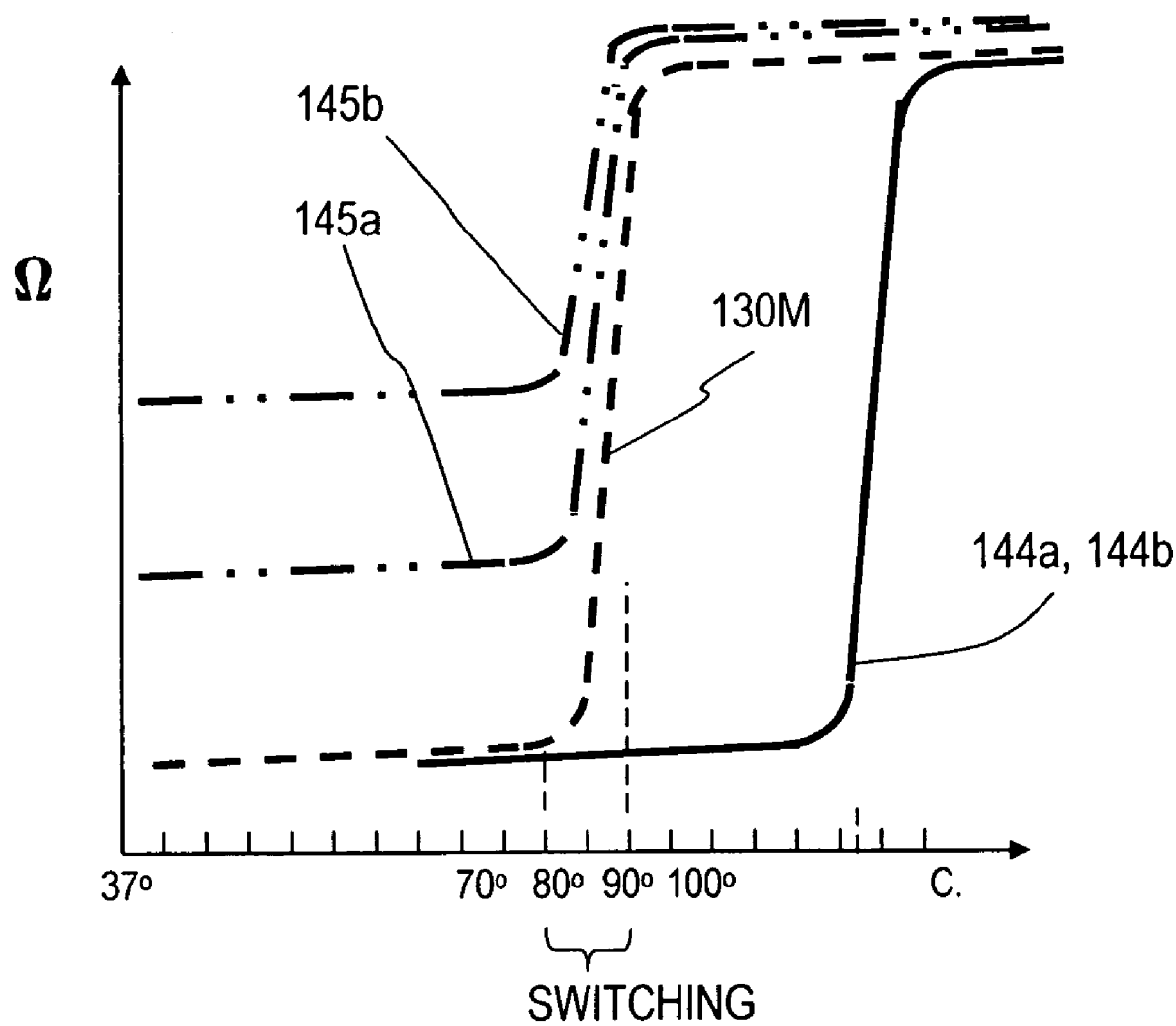
FIG. 4B is a diagram similar to that of FIG. 4A illustrating alternative temperature-impedance curves of variable impedance matrix bodies.

Referring again to FIG. 3, one embodiment of polymer matrix 125 has at least two differentiated regions 144 and 145 that define different temperature-impedance curves as illustrated in FIG. 4B. The regions 144a and 144b (collectively 144) at the center of the lower jaw and the laterally-outward edge of the jaw are of a highly conductive matrix that will only terminate current flow therethrough at a high temperature, for example between 100° C. and 200° C. as shown in FIG. 4B. These regions 144 effectively function as the opposing polarity conductive electrodes as the regions 144 are in contact with the central first polarity conductor 140 and the second polarity jaw body 132A. The lower jaw's matrix region 145 can also provide a plurality of slightly different regions 145a and 145b the have somewhat different base resistances and/or switching ranges as shown in FIG. 4B for reasons described below. In any event, matrix region 145 has a base resistance that somewhat higher than that of matrix 130 in the upper jaw 112B. The jaw structure is coupled to voltage source 150A (a radiofrequency generator) and controller 150B for controlling duration of energy delivery and other RF parameters (FIG. 3). The manner in which matrices 125 and 130 operate to modulate energy densities in tissue will be described in greater detail below.

Figure 5:
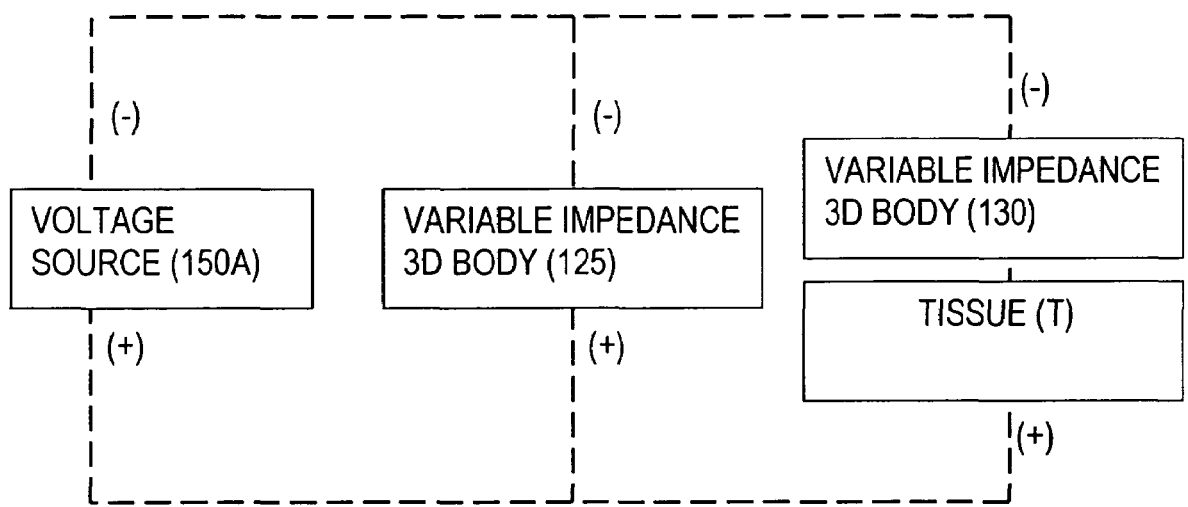
FIG. 5 is a block diagram of the series and parallel electrical circuit components of the working end of FIG. 3.

Of particular interest, the jaw structure 100A corresponding to the invention utilized the two differently performing matrices 125 and 130 (FIG. 3) in combination with the series and parallel circuitry of FIG. 5 to provide effective high and low process limits for temperatures and energy densities in the engaged tissue T. It has been found that such dynamic energy and temperature controls are optimal for creating uniform thermal effects in tissue to denature tissue proteins and to create high strength welds. In one embodiment as in FIG. 3, the matrix 130 in upper jaw 112B is engineered to exhibit unique temperature-impedance characteristics represented by the positively-sloped curve 130M of FIG. 4B. This matrix 130 maintains a relatively low base resistance over a selected base temperature range with a dramatically increases resistance above a selected narrow temperature range (switching range) that can be any 1° to 10° range between about 50° C. and 200° C., and more preferably between about 70° C. and 120° C. In comparison, the matrix region 145 in lower jaw 112A is designed to have an impedance-resistance curve exhibiting a higher initial base resistance (see FIG. 4B). The matrix region 145 provides this higher base resistance over a similar temperature range as matrix 130. The matrix 145 and its temperature-impedance curves (145a, 145b) in FIG. 4B again exhibits a dramatically increasing resistance above its selected switching range, which can fall in the range described previously with reference to matrix 130.

Figure 6:
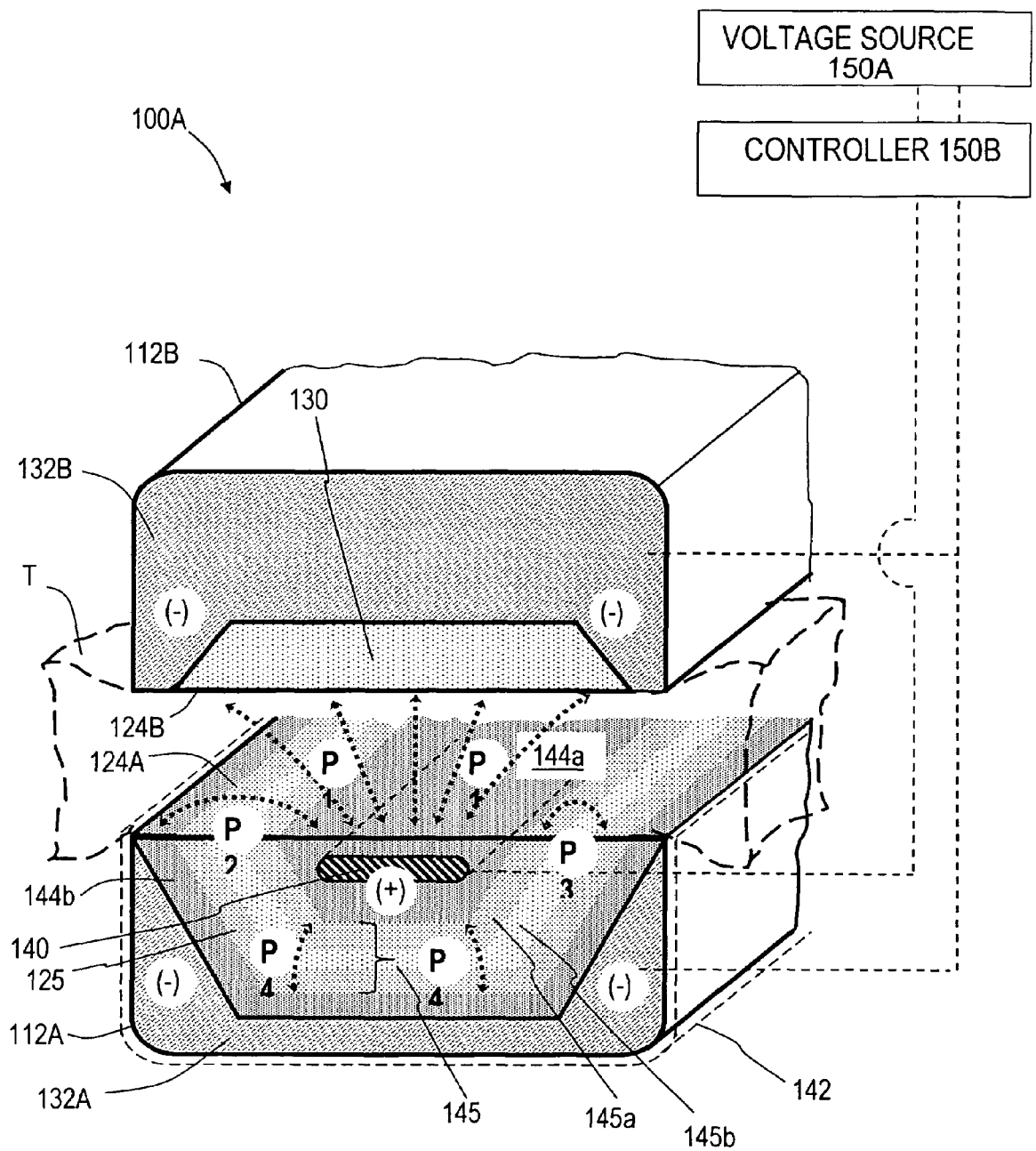
FIG. 6 is a sectional schematic view of the variable impedance matrix bodies showing potential current flow paths in the engaged tissue and the matrix bodies.

FIG. 6 graphically depicts the manner in which the jaw structure 100A of FIGS. 1 and 3 can self-modulate current flow among multiple paths—depending on the temperature of the engaged tissue and other electrical conduction parameters of the tissue to which the matrices 125 and 130 respond. FIG. 6 again depicts a sectional view of the jaws 112A and 112B as in FIG. 3 engaging tissue T in phantom view. In FIG. 6, the tissue thickness is not to scale to allow a graphic representation of potential current paths. In actual operation, the working end 100A of FIG. 6 has the ability to modulate current flow among multiple different paths through the tissue T as well as through the matrices 125 and 130. Current and voltage in the tissue T is modulated after the tissue is ohmically heated—and thereafter heat from the tissue T is transferred by passive conduction to adjacent regions of matrices 125 and 130. While there will exist a multiplicity of potential current paths in the engaged tissue and matrices, FIG. 6 illustrates four different flow paths, P1 through P4, that effectively provide the self-modulating energy control system of the invention. Energy levels in each flow path are dynamic during RF energy delivery to tissue, which will be described in more detail below. In FIG. 6, flow paths P1 indicates potential RF microcurrent flows directly through tissue T between first polarity electrode 140 and conductive region 145 and the low resistance matrix 130 of upper jaw 112B that overlies the (opposing) second polarity jaw body 132B. It can be understood that these current paths P1 provide initial rapid ohmic heating of tissue. Flow paths P2 indicate RF current flow through tissue T between the highly conductive regions 144a and 144b that are laterally spaced apart in the lower jaw that are in contact with first polarity conductor 140 and second polarity jaw body 132A, respectively.

Of particular interest, potential current flow paths indicated at P3 and P4 are unique to the invention and come operate to modulate ohmic heating in engaged tissue as its conductive parameters (impedance, temperature, hydration) are dynamic during energy application. Potential flow paths P3 represent potential microcurrent paths through a region of tissue between spaced apart surface portions of matrix 125 that engage such a tissue region. Potential current flow paths P4 are at an interior of the jaw and the 3D matrix 125 wherein current can flow generally from electrode 140 across the matrix region 145 to the interior of the opposing polarity jaw body 132A. A more detailed step-by-step description of current flow modulation is provided below in the text accompanying FIGS. 10A–10D.

For clarity of explanation, FIG. 6 depicts the principles of the working end in a basic forceps-type jaw structure 100A of FIGS. 1 and 3. It should be appreciated that the same variable impedance matrices 125 and 130 can be provided in a jaw structure indicated at 100B in FIGS. 7 and 8 that carries a blade for transecting the welded tissue. Further, the same variable impedance matrices 125 and 130 can be carried in a one-step jaw structure that is described below (FIGS. 11–12) wherein jaw closing, RF energy delivery and tissue transection occur in a single operation. Now referring to FIGS. 7 and 8, a forceps-type instrument is shown with a detachable cartridge 154 that carries a thin flexible blade member 155 that can be pushed by thumb slider 156 when the jaws are locked in a closed position. Such a blade cartridge was disclosed in co-pending U.S. patent application Ser. No. 10/443,974, filed May 22, 2003 titled Electrosurgical Working End with Replaceable Cartridges which is incorporated herein by this reference.

Figure 7:
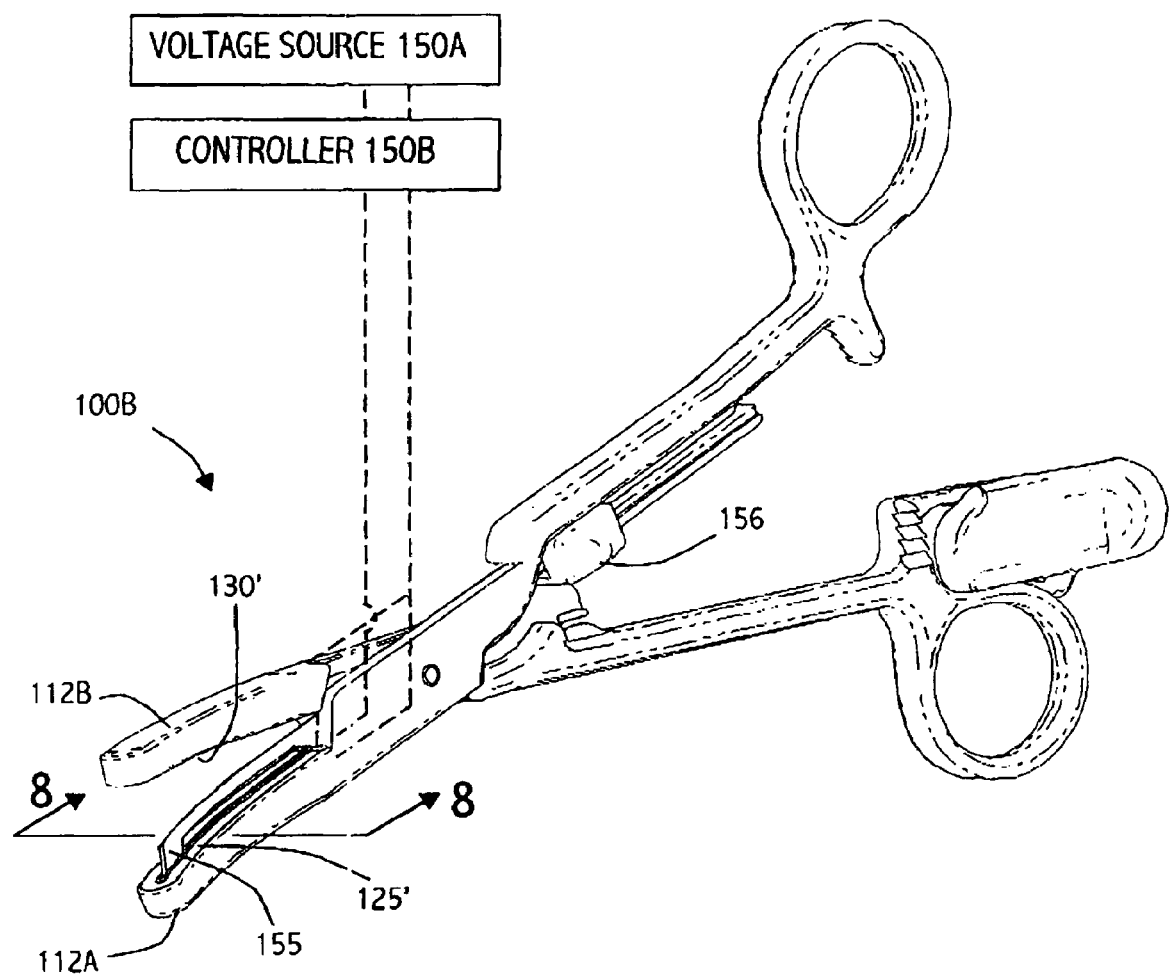
FIG. 7 is a perspective view of an alternative instrument with and a jaw structure carrying variable impedance matrix bodies together with blade means for transecting tissue.
Figure 8:
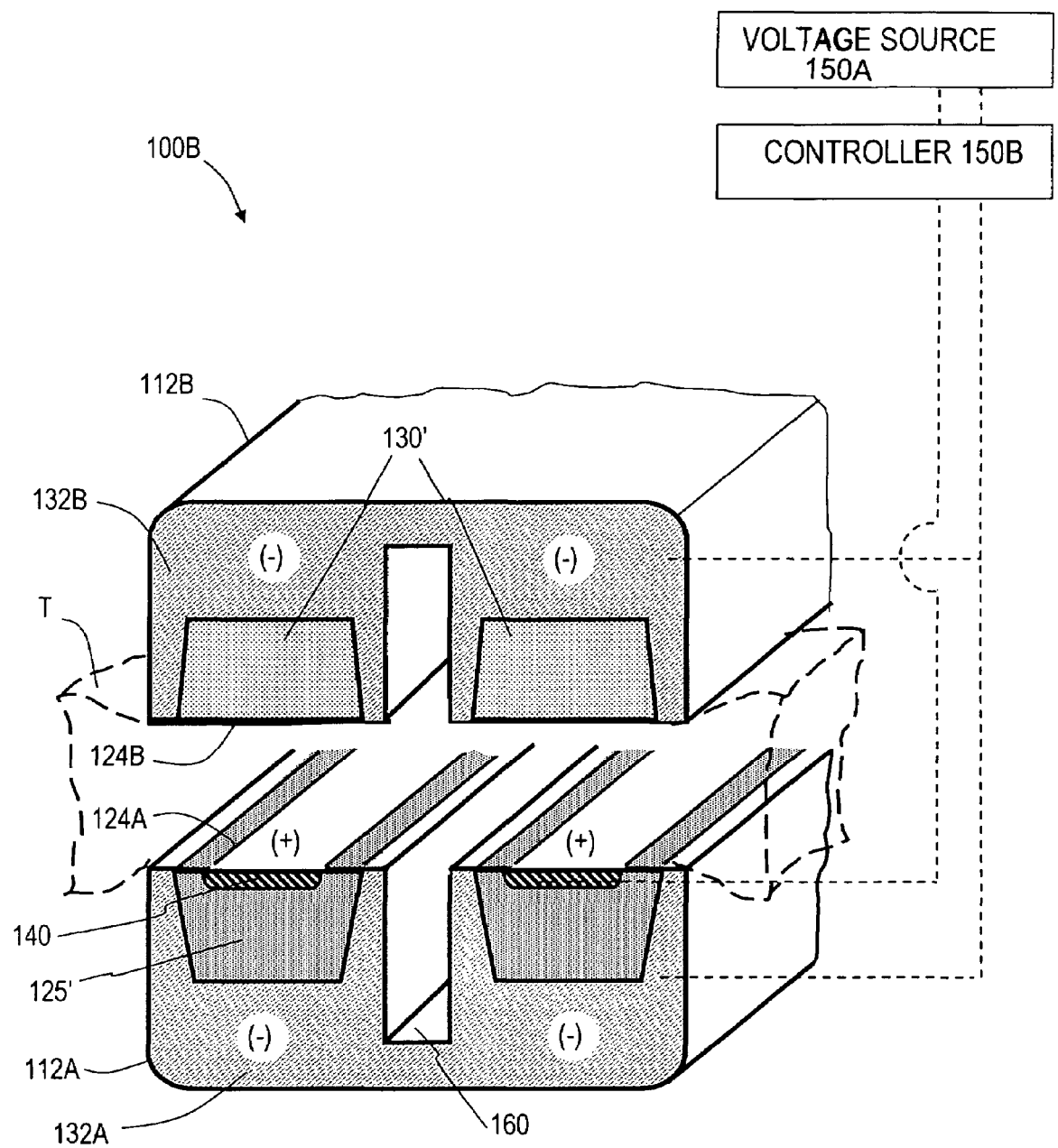
FIG. 8 is a sectional view of the jaw structure of FIG. 7 taken along line 8—8 of FIG. 7 showing the variable impedance matrices in each jaw together blade means.

FIG. 8 illustrates a cross section of the upper and lower jaws 112A and 112B with a central blade slot 160 for receiving the slidable, flexible blade member 155. On either side of the blade slot 160, the jaw bodies carry variable impedance matrices 125' and 130' that are similar (or identical) to the matrices depicted in FIG. 3. In the exemplary embodiment of FIG. 8, the lower jaw 112B has a matrix 125' that is simplified in that electrode 140 is exposed in the center of the jaw's engagement surface 124A with a portion of the 3D matrix 125' extending laterally on either side of blade slot 160 as well as within the interior of the jaw. As can be seen in FIG. 7, matrix extends in a "U"-shape around the end of blade slot 160 to allow welding of engaged tissue around the end of a welded and transected tissue region.

Figure 9:
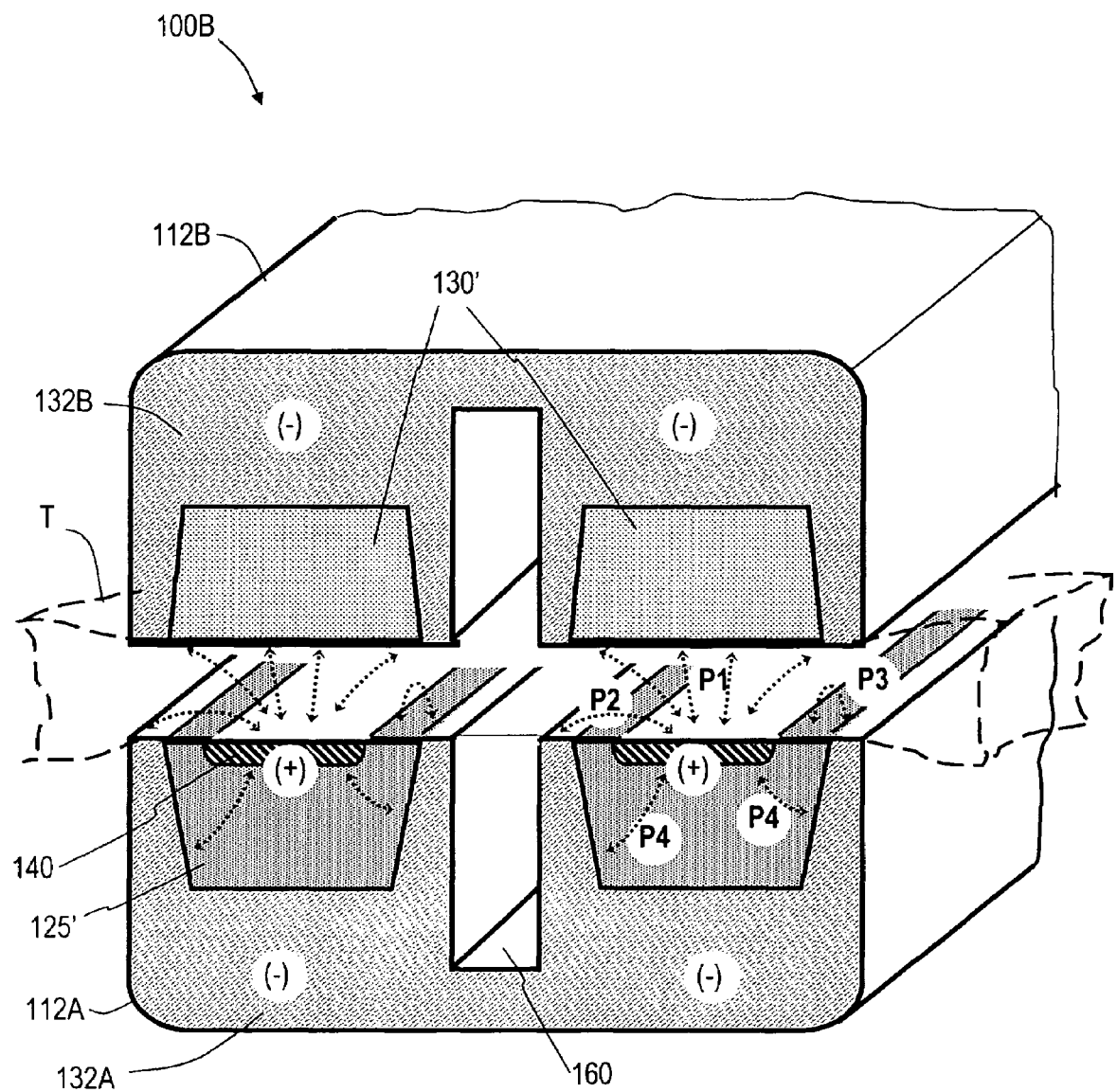
FIG. 9 is a sectional schematic view of the jaw structure of FIGS. 7-8 that illustrates potential current flow paths in the engaged tissue and the matrix bodies.

In all respects, the working end 100B of FIGS. 7–8 functions to modulate RF energy application to tissue in between multiple potential paths as described above and depicted in FIG. 6. FIG. 9 illustrates the working end 100B of FIGS. 7–8 and again graphically depicts the potential RF current paths in tissue and across regions of the variable impedance matrices. The current paths P1, P2 and P3 again represent potential paths in the engaged tissue T. In FIG. 9, the current paths P4 represent paths within the interior regions of matrix 125' between first polarity (+) surface conductor 140 and a second polarity (−) region of jaw body 132A.

Method of utilizing temperature responsive variable impedance matrices for RF modulation. Now turning to FIGS. 10A–10D, the sequential energy delivery phases of the method of the invention is graphically illustrated. In FIGS. 10A–10D, the opposing jaws 112A and 112B are depicted engaging a tissue bundle T, and RF energy application to tissue is modulated by matrices 125 and 130 between various paths P1–P4 in the tissue to create a uniform temperature without desiccation or charring to provide an effective high strength weld. FIGS. 10A–10D illustrate a basic jaw structure 100C similar to that of FIG. without a blade member, but it should be appreciated that a jaw 100B with a reciprocatable blade as in FIGS. 7–8 would create a weld by the same means of energy application and modulation. For clarity of explanation, the engagement surface 124A of FIGS. 10A–10D has the central conductive member or electrode 140 exposed in the surface (cf. FIGS. 7–9).

Figure 10A:
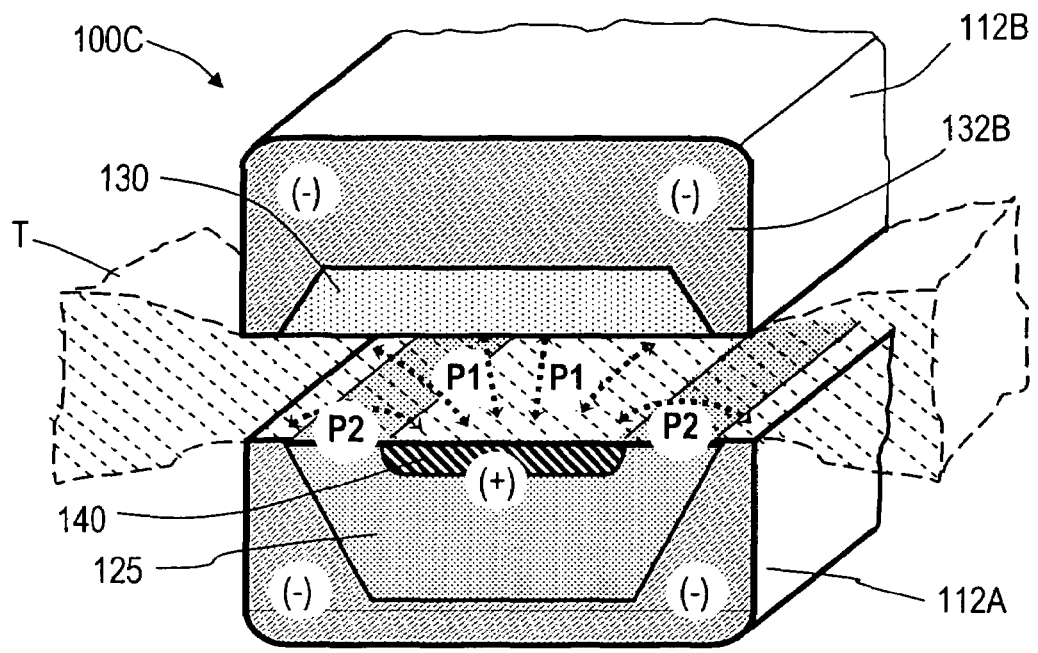
FIG. 10A is a sectional view of the jaw structure of FIGS. 7–8 illustrating an initial step in a method of the invention wherein RF current flow paths cross the engaged tissue to cause ohmic heating therein.

Now turning to FIG. 10A, an initial energy application step is illustrated wherein tissue bundle T is engaged as the jaws apply compression and the surgeon applies RF energy to the tissue. At initiation of RF energy application, FIG. 10A illustrates that current flows are substantially through the tissue between the first polarity conductor 140 and the opposing matrix 130 and laterally-outward upper jaw 132B as well to the second polarity lower jaw body 132A, that is in paths P1 and P2 as depicted in FIGS. 3 and 9. Thus, FIG. 10A depicts current flow that causes very high energy densities and very rapid ohmic heating in the engaged tissue T. In this initial phase of RF energy application to the jaw structure 100C and to the engaged tissue T, the matrices 125 and 130 are, in effect, in a stand-by mode and are not yet operating to modulate flow paths of the microcurrents in the tissue. The matrix 130 in the upper jaw at ambient room temperature has a low base resistance (see FIG. 4B) and allows a multiplicity of conductive flow paths all across and through the matrix 130 to the second polarity jaw body 132B from the first polarity conductor 140 in the lower jaw through the tissue T.

In FIG. 10A, the ohmically heated tissue causes conductive heat transfer to the matrices 125 and 130 to heat at least the surface regions of both matrices. At the same time (see FIG. 10B) the ohmically heated tissue T dehydrates, changes its geometry by shrinking and exhibits an increased impedance. In this phase of energy application, the variable impedance matrix 130 responds according to its selected temperature-impedance curve (see FIG. 4B) wherein the material regulate and modulate flow paths P1 of microcurrents therethrough. For example, the switching range of the matrix can be between about 60° C. to 120° C. and is more preferably in the 70° C. to 90° C., range. During and following this phase, the impedance of tissue regions will be substantially matched by the induced impedance of adjacent regions of matrix 130, to thereby modulate current flow in paths P1 between the jaws. At the same time, the matrix 130 will prevent any possibility of arcs or sparks at the interface of a jaw surfaces 124A and 124B with the engaged tissue since current flow will be eliminated before excessive high temperatures are reached about any region of the tissue-jaw interfaces. The prevention of such arcs eliminates the possibility of unwanted tissue charring.

During this initial energy application phase, the ohmically heated tissue also will conduct heat back to matrix 125 in the lower jaw 112A to elevate the lower matrix above its selected switching range, for example in the 70° C. to 90° C., range. Still referring to FIG. 10A, as the thickness of tissue T is reduced by compression and ohmic-induced dehydration, the increased impedance of the tissue will first prevent microcurrent flows in paths P1 as the upper jaw's matrix 130 is masked. At this point, there will remain the possibility of microcurrent flows in paths P2 between the electrode 140 and the laterally-outward jaw body portion 132A.

Figure 10B:
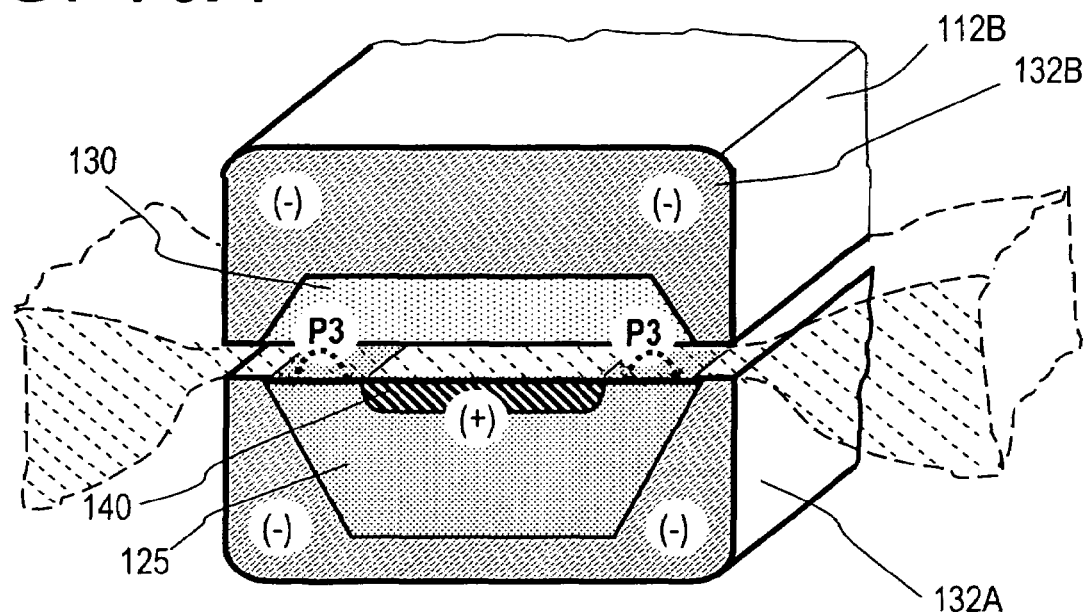
FIG. 10B is a sectional view of the jaw structure of FIG. 10A depicting a subsequent step in a method of the invention with modulated RF current flow paths in the engaged tissue.

Now referring to FIG. 10B, it can be seen that the dehydrated tissue T typically will be compressed to a thin membrane which can increase its impedance in the most direct paths of current (P1 and P2) between the opposing polarity body portions. With the tissue in this condition, the reduction or termination of ohmic heating will cause slight cooling of the tissue and re-hydration of the tissue can occur due to inward fluid migration. In this state, the lower matrix 125 will respond by cooling and then by causing microcurrent flows in paths P3 as indicated in FIG. 10B. Of particular interest, the increase in ohmic heating is then localized is these lateral regions of the engaged tissue while the tissue impedance still masks the upper jaw matrix 130. During this regulated phase of RF energy application, the engaged tissue may hydrates to allow current flows in paths P1 and P2 to cause additional ohmic tissue heating. Thus, it can be understood how the temperature responsive matrices will self-modulate ohmic energy densities in the tissue between the various potential flow paths.

Figure 10C:
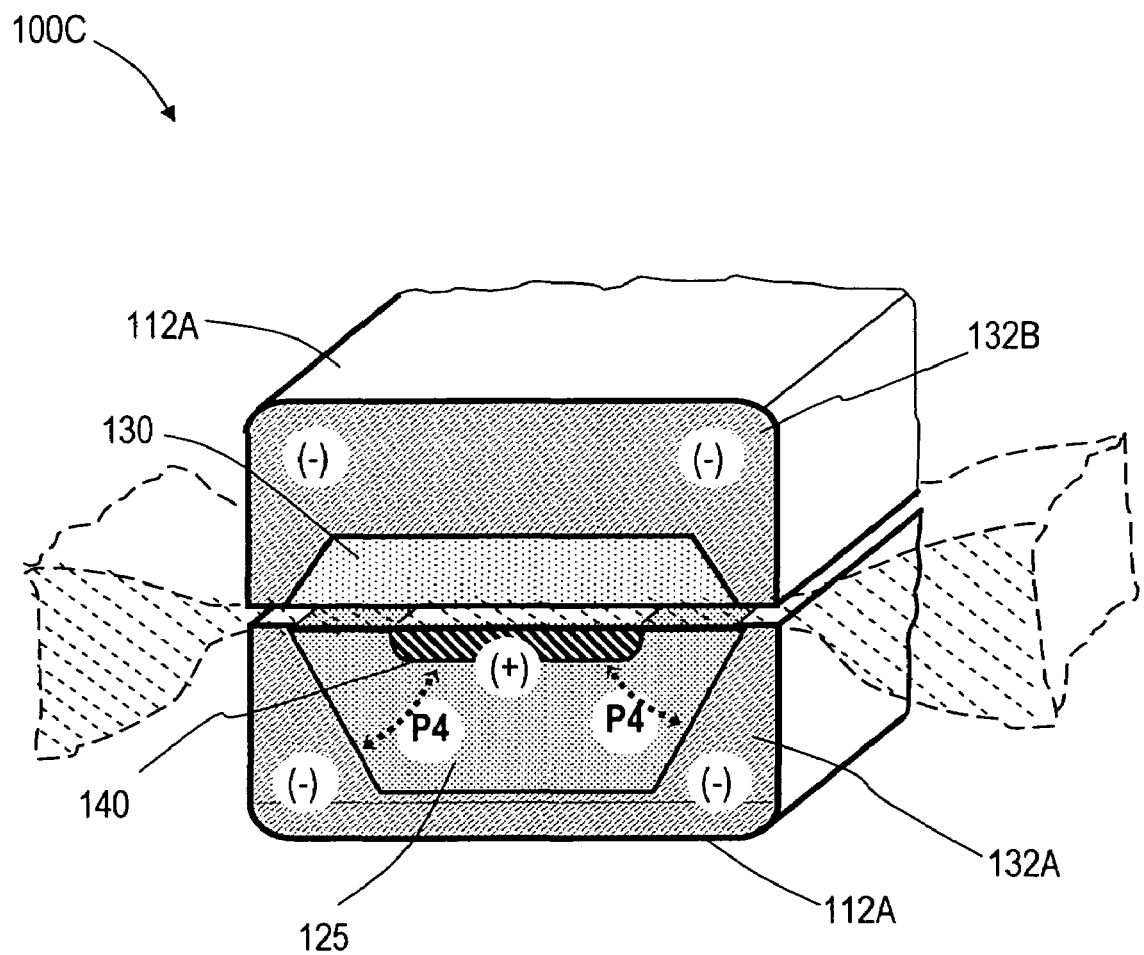
FIG. 10C is another sectional view similar to FIGS. 10A–10B depicting a step in a method of the invention wherein RF current flow paths within an interior of a variable impedance matrix prevent sparking at a jaw engagement surface.

FIG. 10C indicates another potential flow path P4 that can come into play if any voltage occurs that could cause an arc at the jaw-tissue interface. In effect, the energy can be dissipated by energy flows in the paths indicated at P4 between the first polarity conductor 140 and the second polarity lower jaw body 132A directly through the lower matrix 125 at the jaw's interior.

FIGS. 10A–10C indicate generally how the temperature-responsive matrices 125 and 130, at the tissue-engaging surfaces 124A and 124B, will modulate ohmic heating in the engaged adjacent tissue T. It should be appreciated that the energy modulation also occurs about very localized regions of the engaged tissue T that is made up of different tissue types as discussed in the text accompanying FIG. 2. Thus as any local region of tissue impedance changes during ohmic heating, the local adjacent region of matrix 130 in the initial phase will move to an impedance matching level.

Figure 10D:
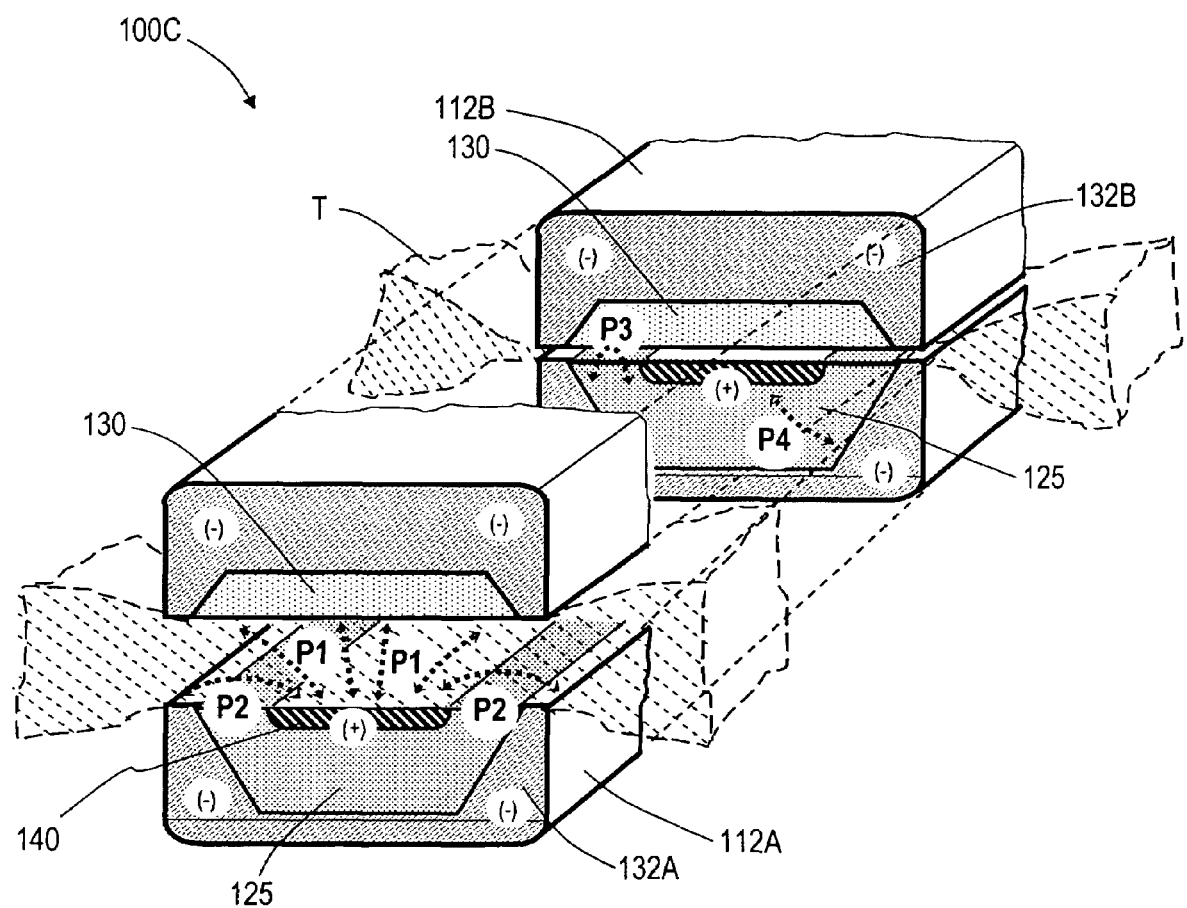
FIG. 10D is another view similar to FIGS. 10A–10C depicting a step in a method of the invention wherein RF current flow paths occur in different axial regions of the jaws depending on local jaw compression.

Further, as described above, the tissue dimension and geometry between the engagement surfaces 124A and 125B of the jaws is dynamic and shrinking during ohmic heating of the tissue T. Thus, the local dynamics of ohmic heating in tissue along the axial length of the jaw can be significant. FIG. 10D illustrates the pivoting jaw structure 100C as applying higher compression to more proximal tissue regions and the jaws close and the tissue dehydrates and shrinks during energy delivery. It can be understood that ohmic heating is thus modulated by matrices 125 and 130 in the jaws' engagement surfaces to provide locally independent energy densities in discrete tissue regions depending on local tissue temperature and impedance—as well as tissue geometry.

It has been found that the system described above can be operated with a pre-set duration of RF energy delivery, wherein energy flow and tissue heating is self-regulated by matrices 125 and 130 to effectively provide high and low process limits for the selected duration of energy application. Depending on selected power levels and selected matrix parameters, duration of energy application to create an effective weld can range between about 1 second and 20 seconds, and more preferably is between about 3 second and 15 seconds.

Figure 11:
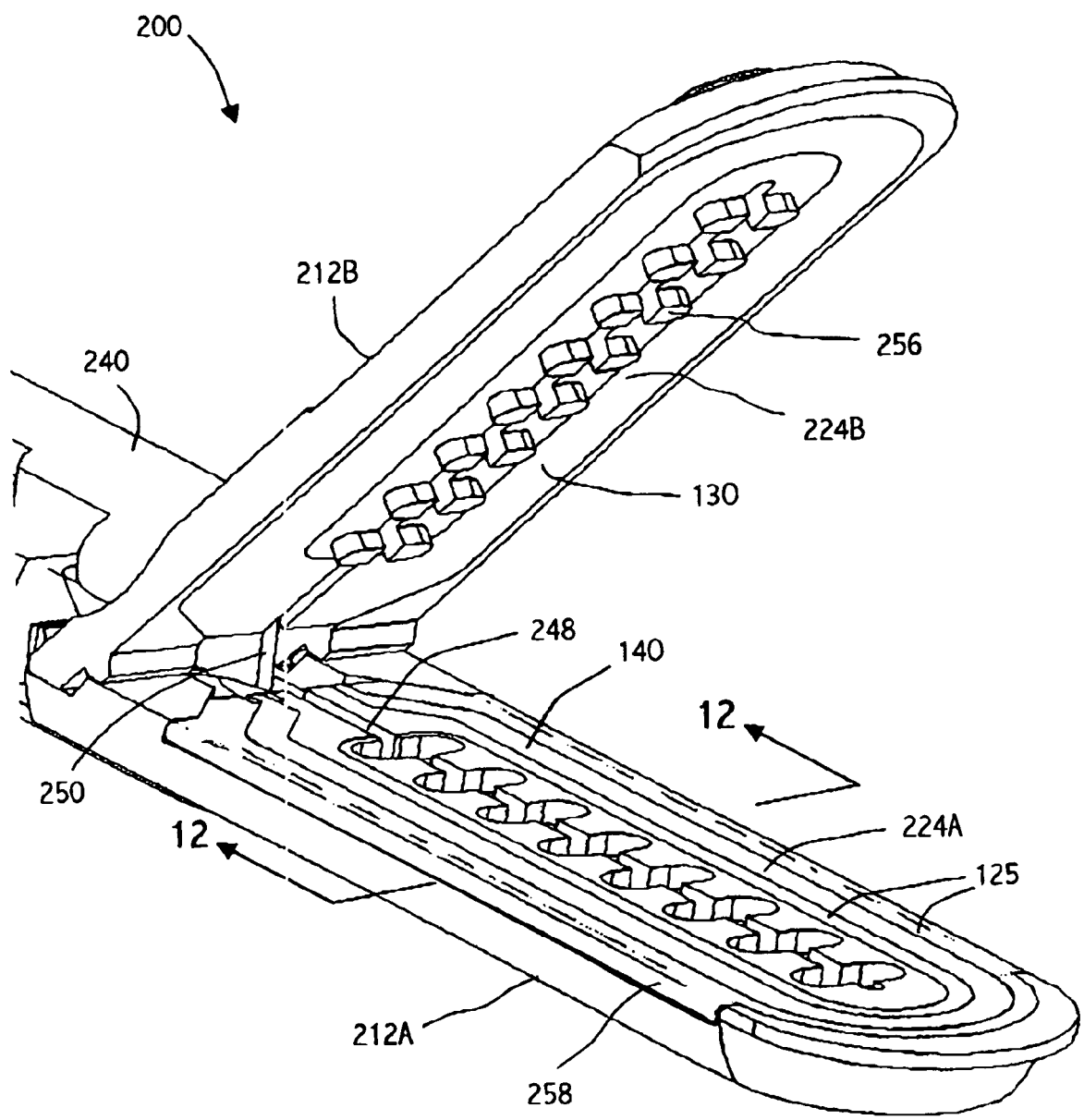
FIG. 11 is a perspective view of an alternative high-compression jaw structure carrying 3D variable impedance matrix bodies that is adapted for one-step tissue welding and transection corresponding to the invention, the matrix bodies coupled to an RF source via series and parallel circuits.
Figure 12:
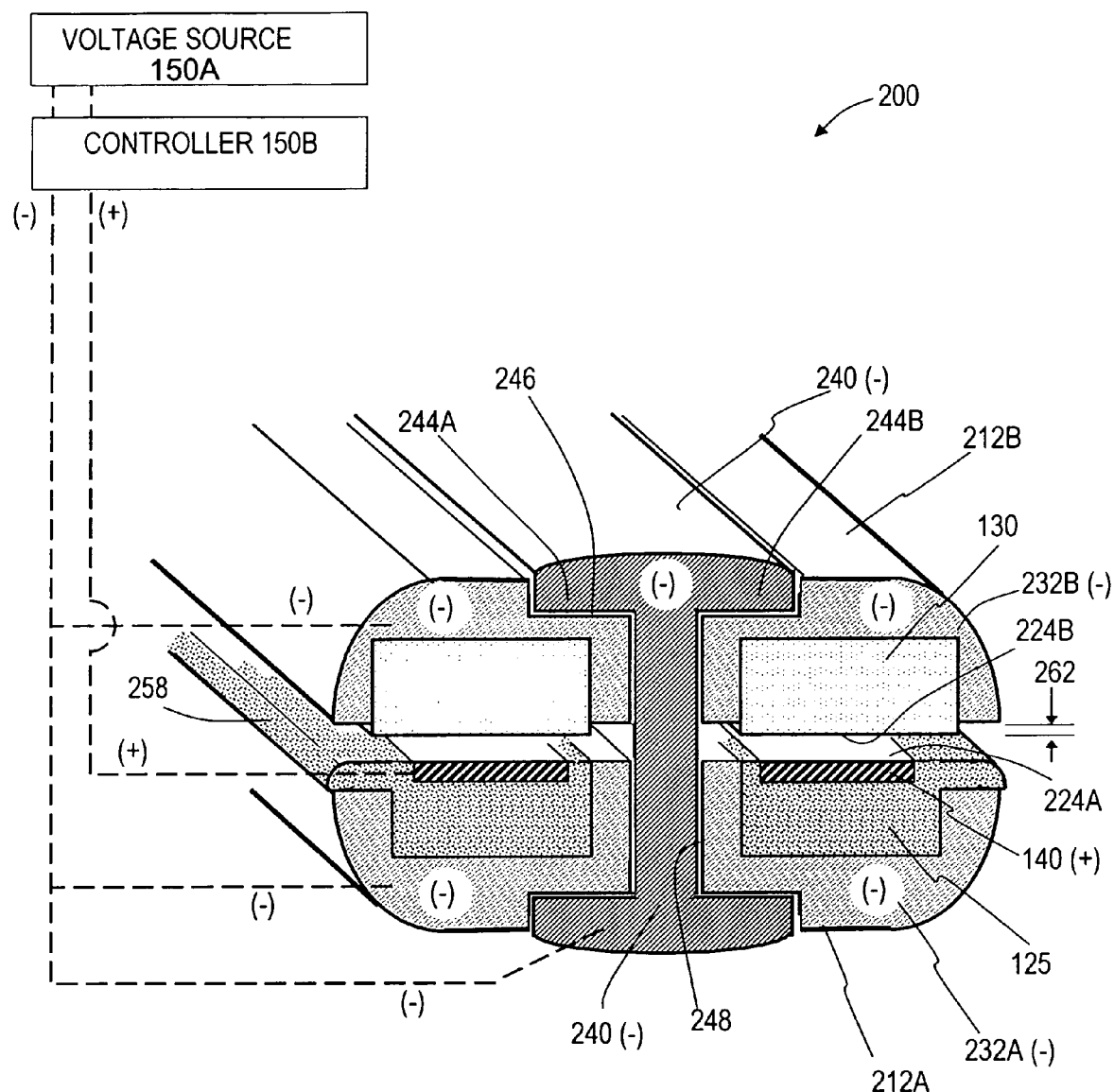
FIG. 12 is a schematic sectional view of the jaw structure of FIG. 11 taken along line 12—12 of FIG. 11 showing the variable impedance matrices in each jaw together with the series and parallel circuits.

Now turning to FIGS. 11 and 12 another embodiment of jaw structure 200 is illustrated that carries cooperating variable impedance matrices as described above. The upper and lower jaws 212A and 212B have respective engagement surfaces 224A and 224B that carry cooperating variable impedance matrices 125 and 130 as in the previous embodiments of FIGS. 3, 6, 8 and 9. The jaw embodiment of FIGS. 11 and 12 differs in that it is adapted for "one-step" welding and transection of the engaged tissue.

In FIGS. 11 and 12, of jaw structure 200 has an opening-closing mechanism that is capable of applying very high compressive forces on tissue on the basis of cam mechanisms with a reciprocating "I"-beam member 240, wherein jaw closing occurs contemporaneous with RF energy delivery. Further, the slidable "I"-beam member 240 and the exterior jaw surfaces provide cam surfaces (i) for moving the jaw assembly to the (second) closed position to apply very high compressive forces, and (ii) for moving the jaws toward the (first) open position to apply substantially high opening forces for dissecting tissue. This feature allows the surgeon to insert the tip of the closed jaws into a dissectable tissue plane—and thereafter open the jaws to apply such dissecting forces against tissues. Many prior art instruments are spring-loaded toward the open position and may not be useful for dissecting tissue.

In the embodiment illustrated in FIGS. 11 and 12, the reciprocating "I"-beam member 240 is actuatable from the handle (not shown) of the instrument by any suitable mechanism, such as a lever arm, that is coupled to a proximal end of member 240. The distal end portion 242 of reciprocating "I"-beam member 240 carries first (lower) and second (upper) continuous laterally-extending flange elements 244A and 244B that are coupled by an intermediate transverse element 245. The flange elements 244A and 244B slide in a recessed slot portion 246 in each of the upper and lower jaws (see FIGS. 12) to close the jaws and wherein the sliding contact of the lateral edges of flanges 244A and 244B and the side of the recessed slot 246 function to prevent lateral flexing of the jaws. The transverse element 245 and blade edge 250 slide within channels 252 (collectively) in the paired first and second jaws 212A and 212B to thereby open and close the jaws. The transverse element 245 is adapted to transect tissue captured between the jaws with a sharp leading blade edge 250 (FIG. 11). In the embodiment, the "I"-beam 240 also is adapted to provide electrosurgical functionality as it transects tissue and has a polarity that matches that of the jaw bodies 232A and 232B which is slidably contacts. The jaw structure of 200 of FIGS. 11 and 12 is described in more complete detail in co-pending U.S. patent application Ser. No. 10/079,728 filed Feb. 19, 2002 titled Electrosurgical Systems and Techniques for Sealing Tissue, and U.S. patent application Ser. No. 10/340,144 filed Jan. 10, 2003 titled Jaw Structure for Electrosurgical Instrument and Method of Use, which are incorporated herein by this reference.

Still referring to FIGS. 11 and 12, the first and second jaws 212A and 212B close about an engagement plane 255 wherein the tissue-engaging surface layers 224A and 224B that contact and deliver energy to engaged tissue T as described above. The jaws can have any suitable length with teeth or serrations 256 for gripping tissue (FIG. 11). One preferred embodiment of FIG. 11 provides such teeth 156 at an inner portion of the jaws along channels 248 thus allowing for substantially smooth engagement surface layers 224A and 224B laterally outward of the tissue-gripping elements. The axial length of jaws 212A and 212B indicated at can be any suitable length depending on the anatomic structure targeted for transection and sealing and typically will range from about 10 mm. to 50 mm. The jaw assembly can apply very high compression over much longer lengths, for example up to about 200 mm., for resecting and sealing organs such as a lung or liver. The scope of the invention also covers jaw assemblies for an instrument used in microsurgeries wherein the jaw length can be about 5.0 mm or less.

Figure 13:
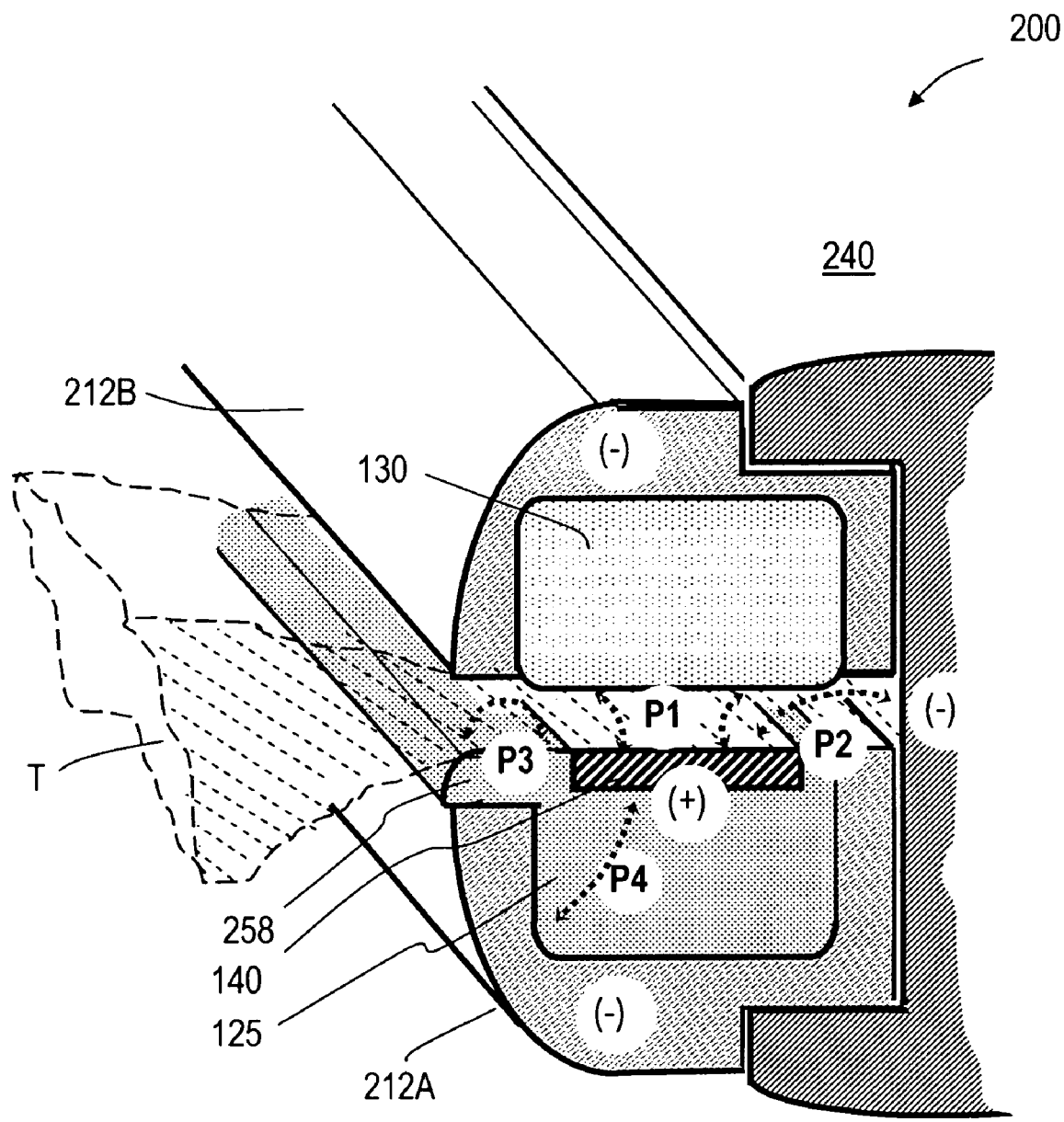
FIG. 13 is an enlarged sectional view of a portion the jaw structure of FIGS. 11–12 showing the potential current paths in engaged tissue and the variable impedance 3D matrix bodies during operation.

In FIGS. 11 and 12, it can be seen that the lower jaw 212A has a variable impedance matrix 125 that has an edge portion 258 that (optionally) extends laterally over the outer edge of the jaw body 232A. This matrix feature has been found useful in modulating RF energy density in the margin of the treated tissue to create distinct region between welded tissue and unaffected tissue. Also, the upper jaw's matrix 130 is positioned to extend slightly outward (dimension 262) from the upper jaw body 232B. FIG. 13 illustrates that the jaw structure 200 of FIGS. 11 and 12 provides the multiplicity of flow paths P1–P4 as described previously in FIGS. 10A–10D. In all other electrosurgical aspects, the jaw structure 200 and variable impedance matrices of FIGS. 11 and 12 function as described above with reference to FIGS. 3, 6, 8, 9 and 10A–10D.

Figure 14A:
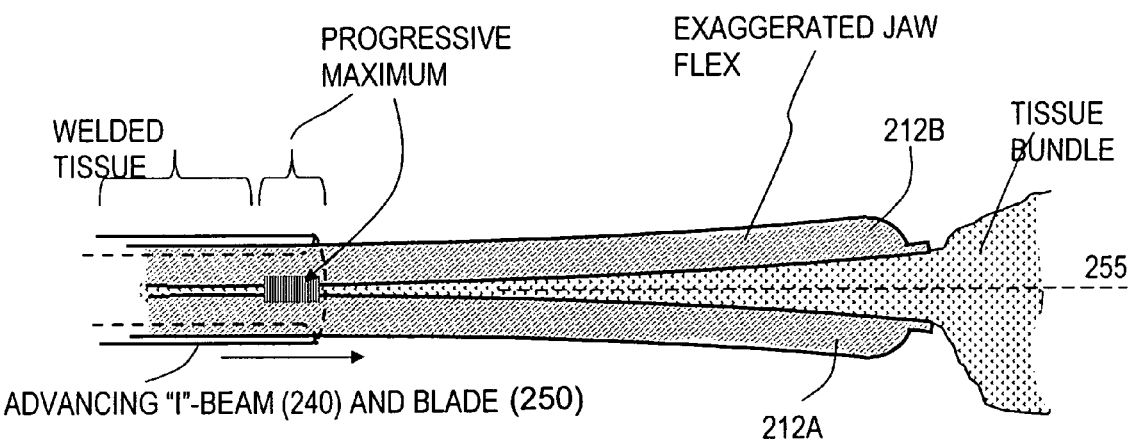
FIGS. 14A–14C are schematic sectional views of the jaw structure of FIGS. 11–13 with elongate jaws progressively engaging, welding and transecting a tissue bundle.
Figure 14B:
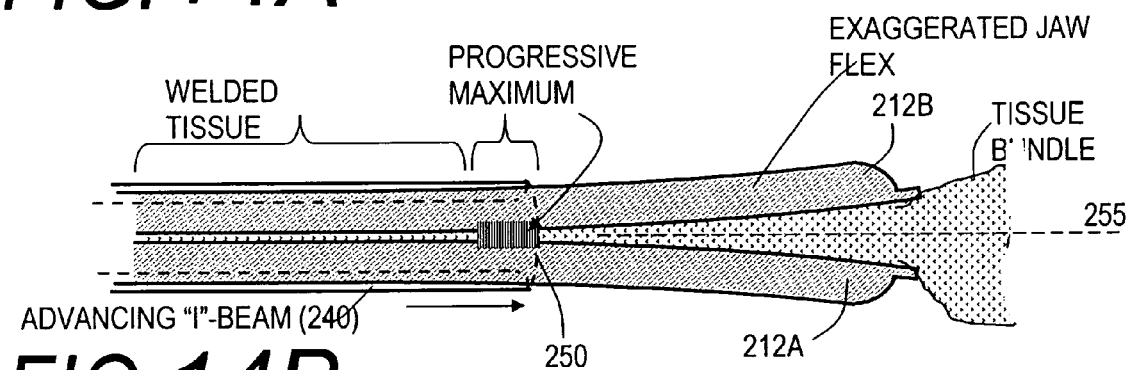
Figure 14C:
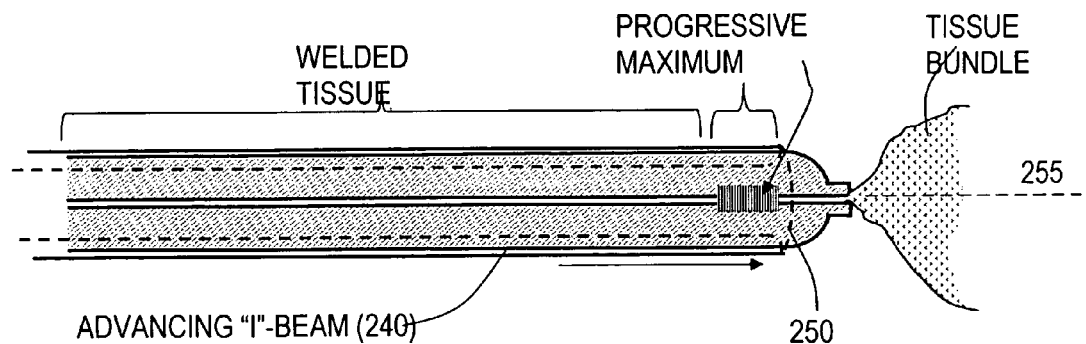

Of particular interest, FIGS. 14A–14C graphically illustrate the one-step sealing and transection method of the invention. When using elongated jaws in a small diameter instrument, the issue of jaw flexure when clamping thick tissue bundles typically creates difficulties for both sealing and transection. The jaw structure 200 of FIGS. 11 and 12 solve such problems by applying RF energy contemporaneously with jaw closure. Initial RF energy delivery will begin to dehydrate the engaged tissue T thus making it possible to compress the tissue to a thin membrane. At the same time, the matrices 125 and 130 will modulate RF ohmic heating axially along the length of the jaws to thereby insure that thin treated tissue regions in the proximal jaw are not being ohmically heated while more distal regions of the engaged tissue are receiving maximal ohmic heating. All the while, each tissue region containing a different tissue type will receive the optimal RF energy density based on impedance matching with the adjacent region of a variable impedance matrix.

In FIGS. 14A–14C, the jaws 212A and 212B are shown with a greatly exaggerated flex characteristics to illustrate, in effect, a method of the invention. The "I"-beam 240 can compress the tissue T dramatically as it is progressively welded. Thus a very small jaw structure 200 in a 5 mm. diameter device can chomp down on, weld and transect very thick tissue bundles, that are initially up to ½ inch or even 1 inch thick. The highest ohmic heating progresses in a "front" across the tissue and is automatically modulated by the variable impedance matrices 125 and 130 and series-parallel circuitry as described above. The jaw structure 200 further allows the surgeon tactile feedback of the tissue welding process as the advancement of the "I"-beam" 240 indicates that the tissue is welded. This inventive method for welding tissue can be most accurately summarized as the microscale modulation of ohmic active heating in engaged tissue as depicted in FIGS. 10A–10D combined with the progressive macroscale application of ohmic heating as in FIGS. 14A–14C as the blade 245 transects the engaged tissue. The one-step welding and transecting functionality is provided by the high compression "I"-beam for jaw closure and tissue transection together with the cooperating variable impedance component 125 and 130 of the jaw structure.

Variable impedance PTC matrix with cooling means. In another electrosurgical system corresponding to the invention, the variable impedance body or PTC composition is provided with cooling means for enhancing the speed of the material's PTC effect and the return to its base resistance. The PTC composition with cooling means, or a heat-subtracting means, can be used in any embodiments of jaw structures that are described above. Also, the PTC composition with cooling means can used in simplified probes for modulating ohmic heating in tissue.

Figure 15:
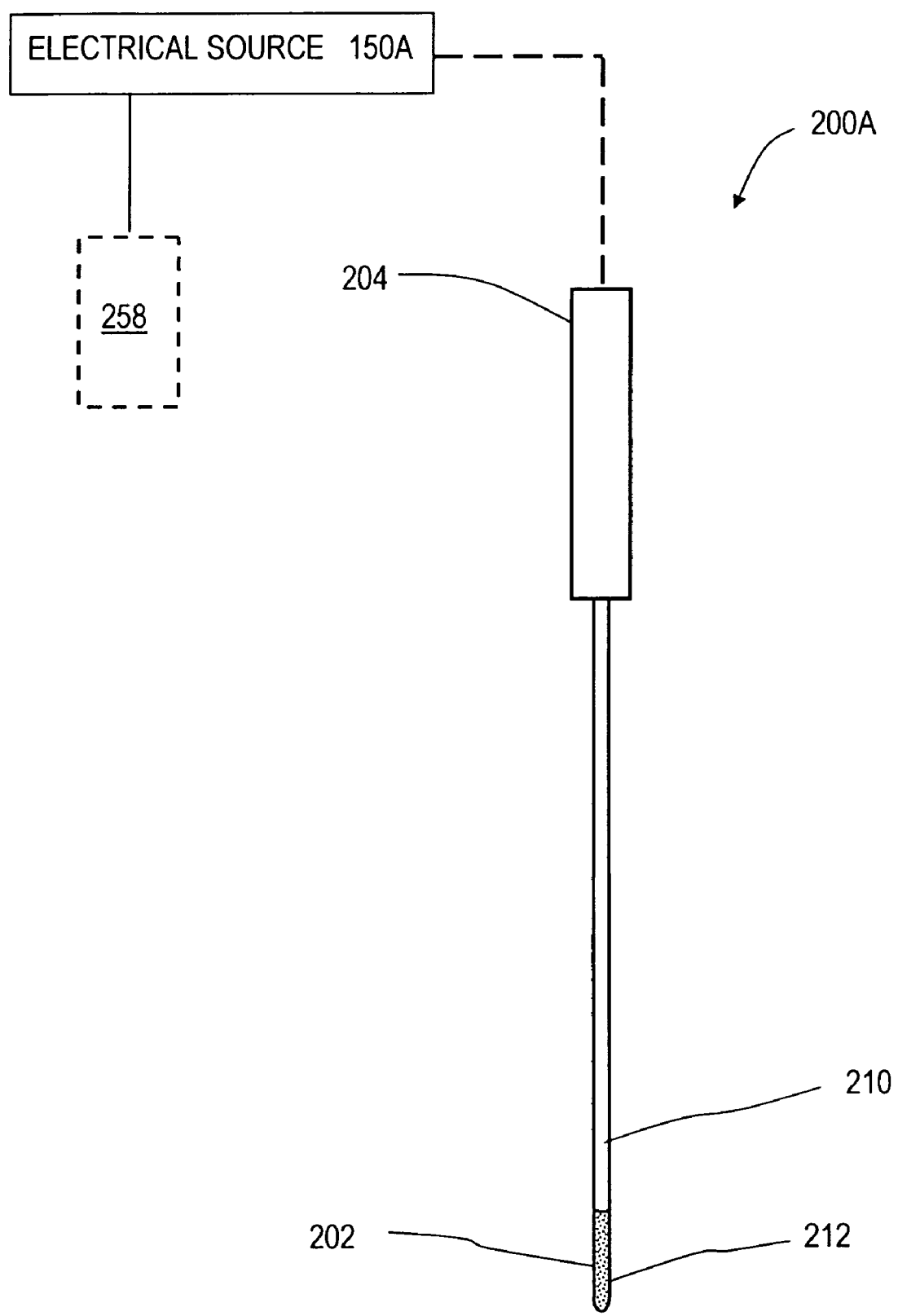
FIG. 15 is a view of a probe-type instrument corresponding to the invention that has a thin conductive-resistive PTC surface layer together with means for subtracting heat from the PTC layer.
Figure 16:
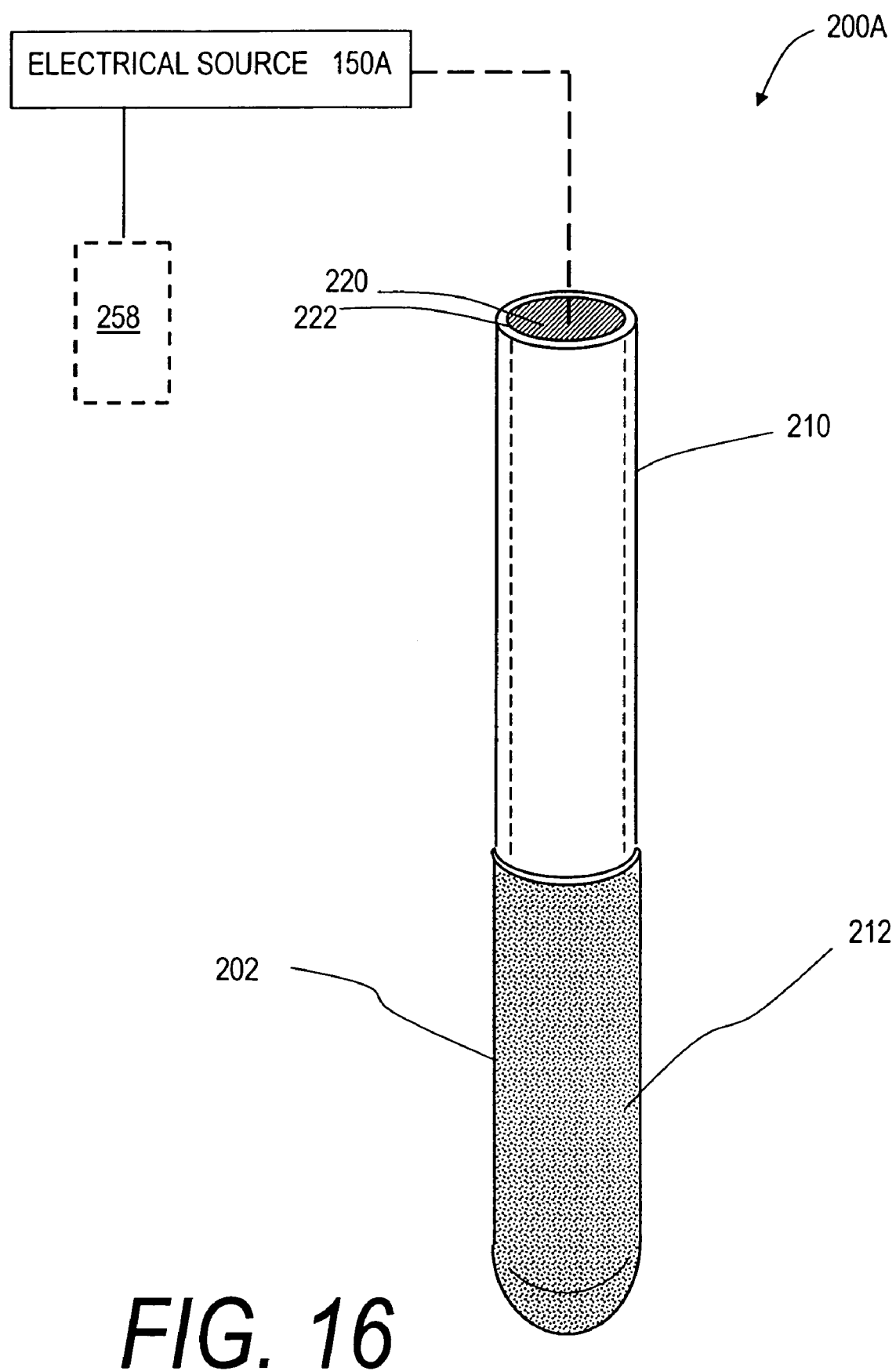
FIG. 16 is a cut-away perspective view of the working end of the instrument of FIG. 15.

In order to provide a clear understanding of the PTC system, the invention and its method of use are first described in a probe-type instrument. FIGS. 15 and 16 illustrate an exemplary probe 200A that has a blunt tip that carries a PTC surface layer 202. This type of probe can be used for painting the tip across synovial tissue to cause ohmic heating and shrinkage of collagen to tighten a joint capsule. As can be seen in FIG. 15, the probe 200A has a proximal handle portion 204 that extends to introducer portion 210 and working end 212. The introducer portion 210 has any suitable diameter ranging from about 1 mm. to 5 mm (not limiting). The probe 200A has a conductive-resistive matrix or PTC surface layer 202 at its distal working surface similar to the matrices described above, with the matrix coupled to an electrical source 150A.

In a probe for shrinking joint capsule tissue, the PTC matrix is designed to have a switching range or PTC effect in the range of about 65° C. to 80° C. In one embodiment, the polymer base material of the matrix 202 can be a high density polyethylene (HDP), a mixture of HDP and a linear low density polyethylene, Nylon 66, Nylon 6,6, Nylon 11, Nylon 12, a polyurethane, silicone or Teflon. The polymer base material is doped with about 50–60 percent carbon particles. The mechanical and chemical properties of the base polymer also can be optimized for the method of the invention by providing filler particles of an anti-oxidant such as titanium oxide or magnesium oxide. The matrix also can be pultruded, mixed or otherwise processed with reinforcing fibers therein that can be electrically conductive with the fibers oriented for reinforcing the strength of the thin matrix as well as for providing for a PTC effect. Further, the base polymer or co-polymers of the PTC layer 202 can be cross-linked by gamma or E-beam radiation.

The probe 200A has a PTC matrix 202 that differs from the conductive-resistive matrix described above in that with the probe of FIGS. 15 and 16 are designed to insure that the thermal switching functionality of the PTC matrix 202 occurs about the very surface of the engagement surface 225 of the working end. One objective of the invention is to provide a PTC matrix that is ideal for localized or pixelated switching between conductive and non-conductive states in respond to the temperature of engaged tissue. It has been found that a polymeric PTC layer that is adapted to cool rapidly after a local portion exceeds its switching temperature will allow for much greater control of ohmic heating in the targeted tissue. Several means have been developed for enhancing the rate of cooling of a PTC layer that engages tissue. In one embodiment, it has been found that passive or active cooling mechanisms operating in conjunction with the PTC matrix will allow the use of a substantially thin matrix layer for an electrosurgical tissue-contacting surface, which in turn will allow a very precise switching range and rapid modulation of energy delivery for ohmic heating in the tissue.

As described above, the PTC matrix is typically fabricated of a base polymer that in a melted state is intermixed with conductive particles. In any manufacturing process in which the conductive particles have a mean diameter in the nanometer range, there can be non-uniform mixing of the conductive particles across the matrix. When making probes that have substantially thin PTC surfaces, it has been found that non-uniformities in the matrix of the polymer and conductive particles can lead to voltage breakdown of the matrix at high voltages. For example, it has been found that matrices exhibit a voltage breakdown in the range of about 25 to 100 volts per 25 microns of matrix thickness. The term voltage breakdown is used herein to describe the irreversible internal breakdown of the matrix composition to cause a short across the matrix. For example, the conductive elements fuse together to provide a permanent current path across the matrix or the polymer melts to cause a short or irreversible resistance to current flow.

In many embodiments of probes and jaw engagement surfaces, it may be possible to make the PTC matrix thick enough to insure that term voltage breakdown does not occur at the required voltage for the targeted thermotherapy, together with additional thickness to provide any desired margin of safety. Using the above range of breakdown voltages, a PTC matrix that is about 250 microns thick would only breakdown in the range of 250 to 1000 volts, which would provide a margin of safety for many procedures that only require about 100 volts or less.

In some embodiments, it is advantageous to provide probes and systems that can operate with very thin PTC matrices, for example, in small diameter instruments and in instruments requiring very precise switching temperatures. For this reason, probe 200A provides mechanisms for maintaining a very thin PTC matrix at a selected temperature that inhibits or prevents any portion of the thin matrix from being subject to voltage breakdown during use.

Figure 17:
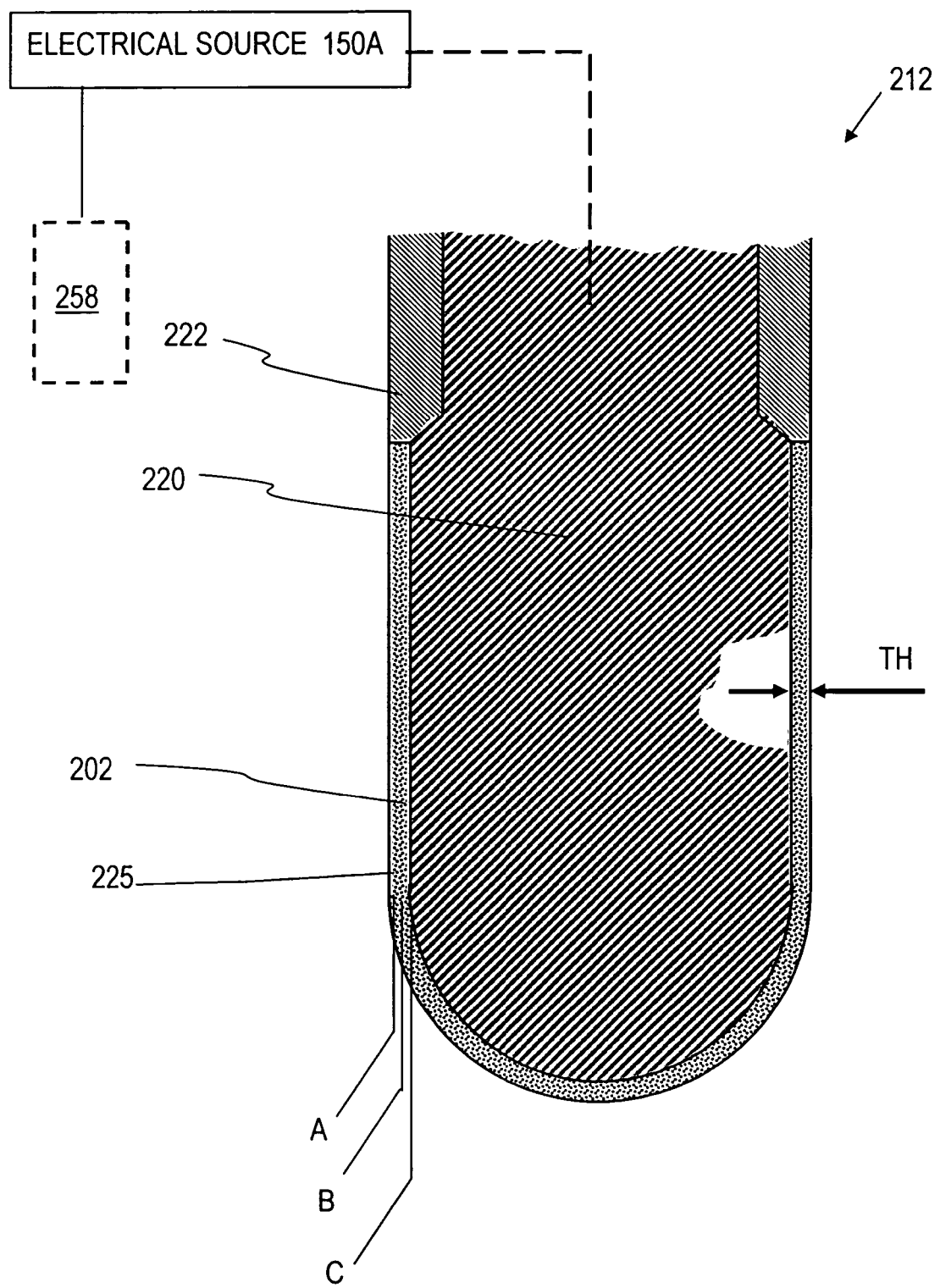
FIG. 17 is an enlarged sectional view of the working end of FIG. 16.

Referring to FIGS. 16–17, one embodiment of working end 212 has an interior conductor 220 with an insulator coating 222 over the introducer member 210. The central electrically conductive portion 220 (or electrode) is a material such as a copper beryllium alloy, copper, aluminum, silver, gold or any other material that is electrically conductive and also has excellent heat sink properties. The interior of the working end may be hollow with a bore (not shown) wherein the hollow bore can carry heat away from the central conductive portion 220. In this embodiment, the working end 212 carries a PTC matrix 202 that defines the engagement surface 225 wherein the matrix has a thickness indicated at TH in FIG. 17 that is less than about 500 microns. More preferably, the PTC matrix 202 that has a thickness TH that is between about 0.1 microns and 200 microns. Still more preferably, the matrix 202 that has a thickness TH that is between about 0.5 microns and 100 microns.

The sectional view of FIG. 17 illustrates the probe with a thin matrix 202 relative to the substantially large cross-section of the heat sink conductor-electrode 220. In operation, it can be easily understood that the probe of FIGS. 15–17 can be used in a mono-polar mode with a cooperating ground pad 258 to paint across a surface of tissue T. The engagement surface 225 in contact with tissue will cause ohmic heating in the tissue which will be conducted back to the probe's surface. In turn, the elevation of any local portion of the matrix 202 to a temperature above its switching range will terminate current flow therethrough. Contemporaneously, the larger cross-section of the heat sink conductive portion 220 will passively subtract heat from localized matrix portions in contact with tissue to thereby cause these matrix portions to rapidly drop in temperature. The use of a central passive heat sink will make the probe's engagement surface highly responsive to local tissue temperatures to, in turn, more precisely modulate ohmic heating and temperatures of localized tissue region at any targeted temperature range.

Figure 18:
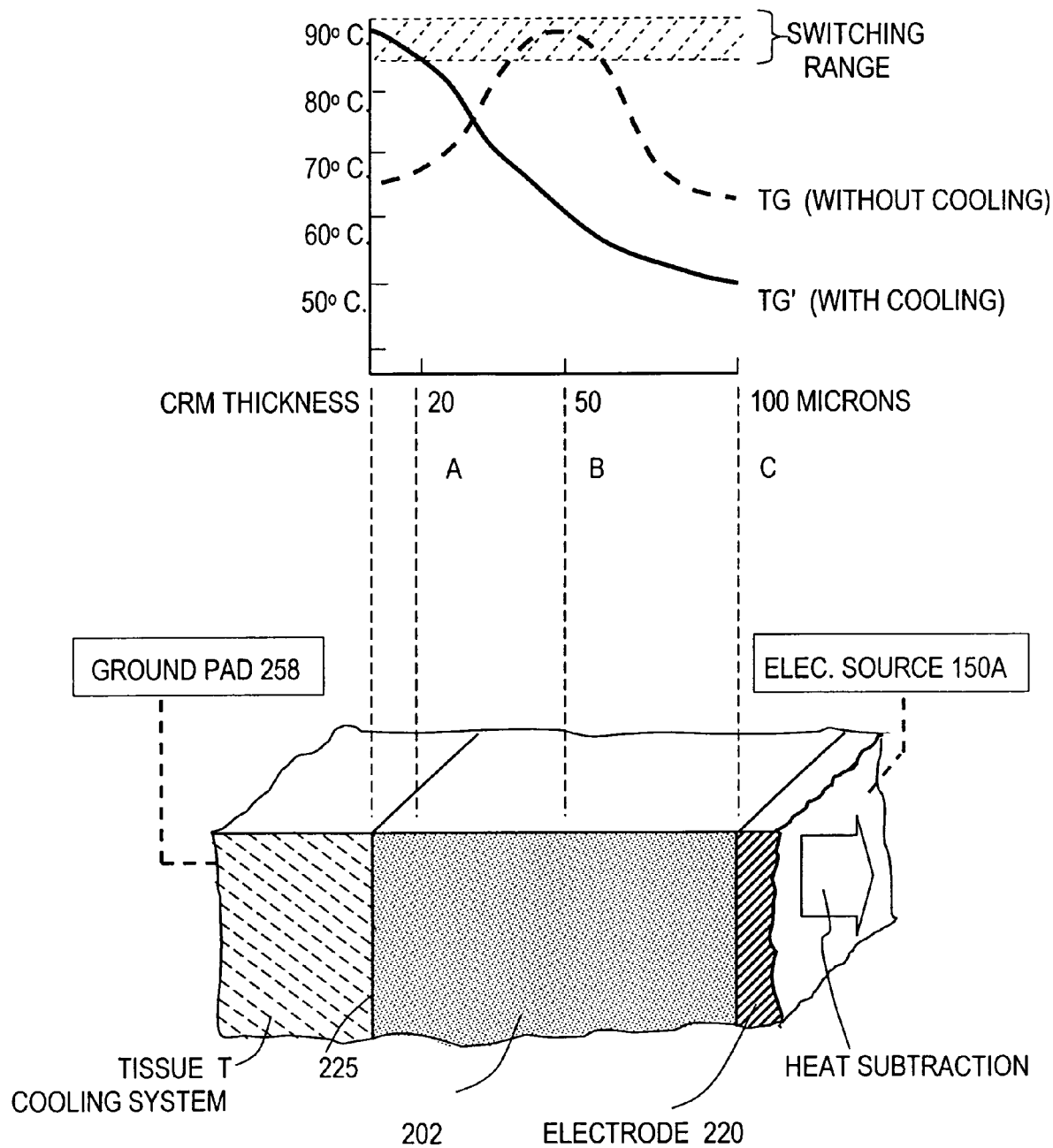
FIG. 18 is a graph of the thermal gradient across the PTC surface layer of FIG. 17 during use.

FIGS. 17 and 18 together illustrate the functionality of the PTC matrix 202 and its ability to maintain the switching functionality at the surface of the matrix. In FIG. 17, the PTC matrix 202 has an exemplary thickness TH of 100 microns, with various depths of the matrix indicated at A, B and C corresponding to 20 microns, 50 microns and 100 microns, respectively. FIG. 18 next shows a sectional view of the PTC matrix 202 and tissue T together with a temperature gradient chart across the depth of the matrix 202 when used with a heat subtracting technology. FIG. 18 further illustrates, in a dashed line, the temperature gradient of an exemplary PTC matrix that does not use a heat subtracting technology. The graph of FIG. 18 shows temperature on its vertical axis and the thickness and depths A, B and C (20, 50 and 100 microns, respectively) of the matrix on the horizontal axis which corresponds to the matrix depths indicated in FIG. 18. An exemplary switching range between 85° C. and 90° C. is shown on the vertical axis of the graph in FIG. 18.

In FIG. 18, a first temperature profile indicated at TG depicts the temperature across various depths of a PTC matrix 202 without a system for active or passive cooling of the matrix when applying energy to tissue. A second temperature profile TG' depicts the temperature profile across a 100 micron thick matrix CRM with a heat subtraction technology corresponding to the invention. With reference to temperature profile TG', it can be seen that a cooling system or heat sink at an interior of electrical conductor 220 will subtract heat from the interior depths of PTC matrix 202 while at the same time the surface 20 microns of the matrix 202 is within the switching range. This is to be contrasted with temperature profile TG wherein the interior region of the matrix may be at the switching range while the surface of the PTC matrix may fall below the switching range. Thus, it can be understood by temperature profile TG' that a passively or actively cooled PTC matrix 202 will enhance the speed of modulation of ohmic heating within tissue T by causing the matrix switching functionality to be localized and controlled in the very thin matrix layers at the engagement plane 225.

Figure 19:
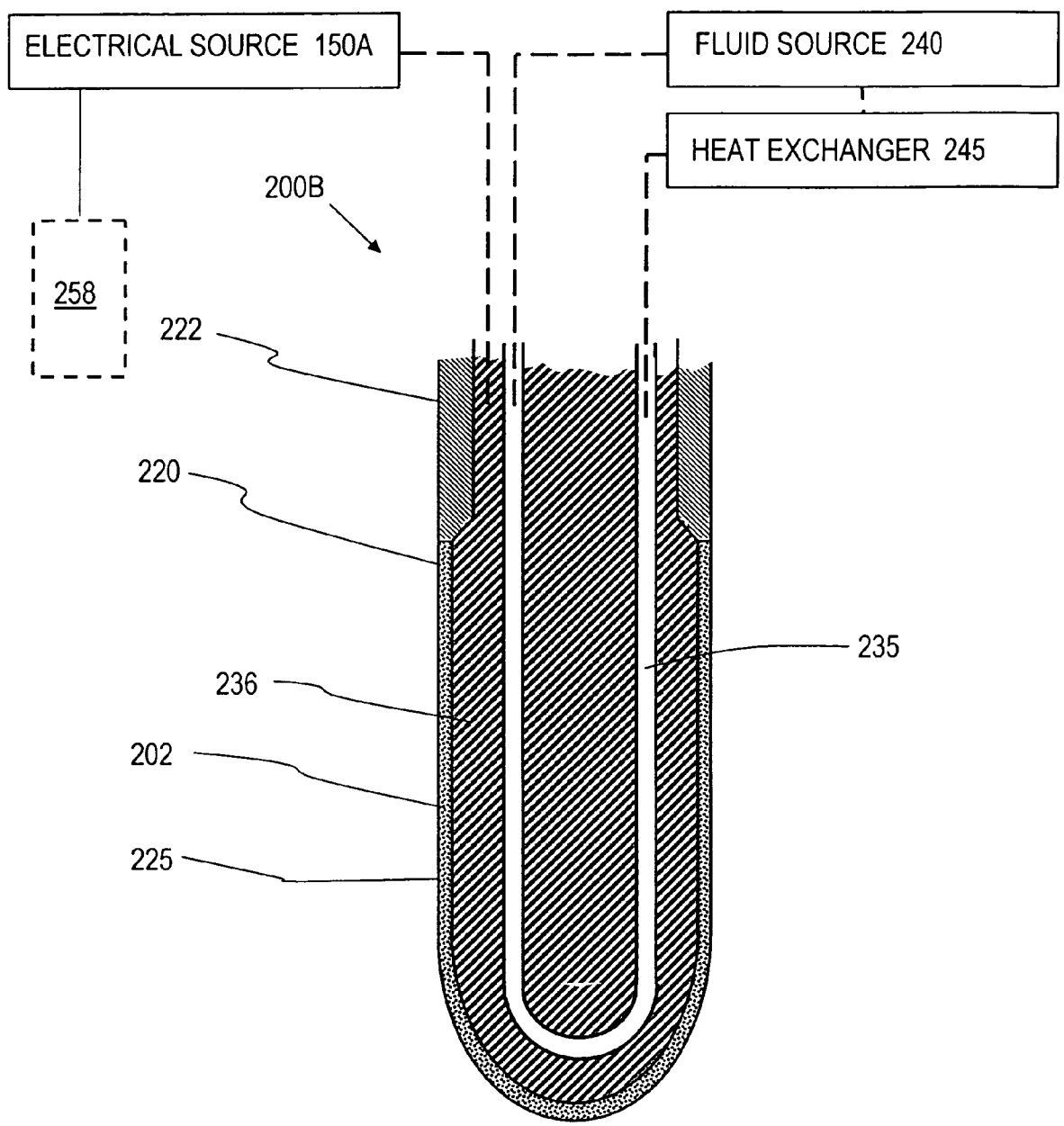
FIG. 19 is a sectional view of an alternative working end with fluid flow cooling means adjacent the thin PTC surface layer.

FIG. 19 illustrates another probe 200B that functions as the probe 200A of FIGS. 15, 16 and 17, except that the probe of FIG. 19 carries an active cooling mechanism for enhancing the heat sink effect of the probe's interior for subtracting heat from the PTC matrix 202. In the exemplary embodiment of FIG. 19, the interior electrical conductor 220 again can be a copper-beryllium alloy or another suitable material with at least one fluid flow channel 235 extending through a distal portion 236 of the conductor 220 to provide a fluid flow loop. The probe 220B is coupled to a fluid source 240 that flows a fluid media through the device as is known in the art to cool the distal conductor portion 236 and the PTC matrix. In one embodiment, a closed fluid flow system pumps the fluid media through a heat exchanger indicated at 245. In another embodiment, a fluid such as water can flow through the system one time to cool the probe with the water then being discharged from the system. In another similar embodiment (not shown) the fluid flow loop for a cooling fluid can be carried within a thicker PTC matrix 202 rather than within the interior conductor 220 of the probe.

Figure 20:
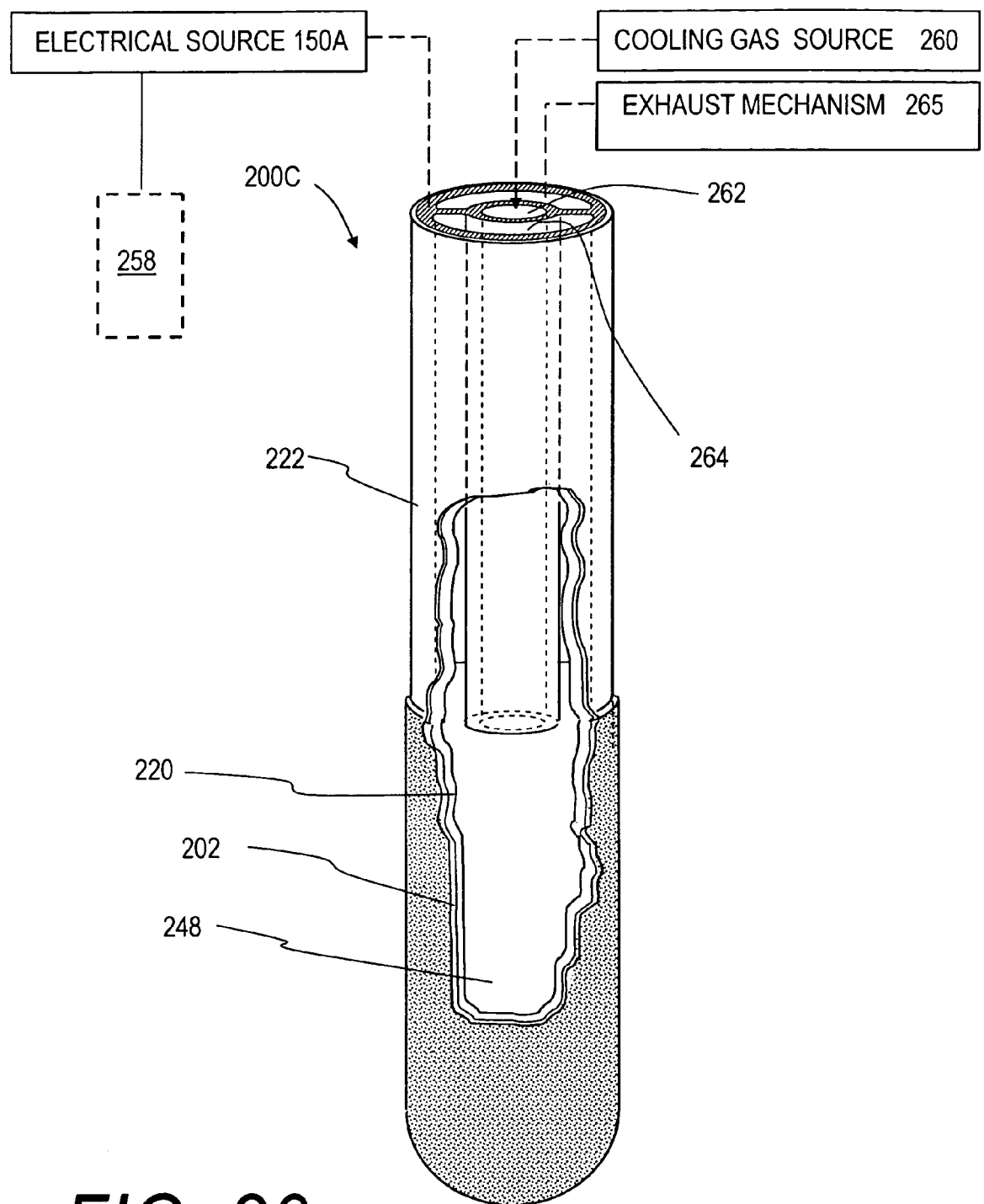
FIG. 20 is a sectional view of an alternative working end with cooling means adjacent the thin PTC surface layer comprising a cryogenic or gas cooling system.

FIG. 20 illustrates an alternative probe 200C corresponding to the invention wherein the interior of the probe working end carries an active cooling mechanism that utilizes any cooling gas, for example cryogen, freon, $CO_2$ or another gas than absorbs heat as it undergoes a phase state change in an interior chamber 248 of the working end. The chamber 248 is adjacent a conductor wall portion 220. A gas source indicated at 260 communicates with inflow channel 262 to deliver the gas to the expansion chamber 248. A gas outflow channel 264 communicates with an optional exhaust mechanism 265 to remove the gas from the working end. It can easily be understood how the gas cooling system can very rapidly lower the temperature of the PTC matrix 202 during use.

In another similar embodiment (not shown), the interior of the probe can carry thermoelectric cooling means also known as Peltier elements. Such thermoelectric cooling elements can be designed by TELLUREX CORP., 1248 Hastings Street, Traverse City, Mich. 49686.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. An electrosurgical instrument for delivering energy to tissue, comprising:
    a working end for engaging the tissue;
    a surface layer at an exterior portion of the working end, the surface layer comprising a matrix of polymeric PTC composition adapted to deliver electrical current to the tissue; and
    a cooling structure at an interior portion of the working end;
    wherein the cooling structure cools the PTC matrix to lower the temperature of one or more portions of the PTC matrix.

2. The electrosurgical instrument of claim 1, wherein the PTC matrix defines a switching range at which the electrical resistance substantially increases in a selected temperature range.

3. The electrosurgical instrument of claim 2, wherein the surface layer has a thickness of less than about 500 microns.

4. The electrosurgical instrument of claim 3, wherein the surface layer has a thickness ranging between about 0.1 microns and 200 microns.

5. The electrosurgical instrument of claim 4, wherein the surface layer has a thickness ranging between about 0.5 microns and 100 microns.

6. The electrosurgical instrument of claim 1, wherein the cooling structure passively cools the PTC matrix.

7. The electrosurgical instrument of claim 6, wherein the cooling structure comprises a thermally conductive material forming an electrode which conducts electrical current from a power source to the PTC matrix.

8. The electrosurgical instrument of claim 7, wherein the cross-section of the conductive portion is significantly larger than the PTC surface layer.

9. The electrosurgical instrument of claim 7, wherein the cooling structure comprises a material selected from a group consisting of copper-beryllium alloy, copper, aluminum, silver, or gold.

10. The electrosurgical instrument of claim 7, further comprising a ground electrode, and wherein the power is supplied to the thermally conductive electrode in a monopolar configuration.

11. The electrosurgical instrument of claim 1, wherein the cooling structure actively cools the PTC matrix.

12. The electrosurgical instrument of claim 11, wherein the cooling structure communicates with a fluid-cooling circulation system.

13. The electrosurgical instrument of claim 12, further comprising a fluid source, wherein the cooling structure has a flow channel to form a flow loop through which the fluid source circulates a fluid.

14. The electrosurgical instrument of claim 13, further comprising a heat exchanger, wherein the fluid pump circulates the fluid through the heat exchanger.

15. The electrosurgical instrument of claim 13, wherein the fluid comprises water.

16. The electrosurgical instrument of claim 13, wherein the fluid comprises a cooling gas.

17. The electrosurgical instrument of claim 16, wherein the cooling gas comprises a cryogen selected from the group consisting of freon or $CO_2$.

18. The electrosurgical instrument of claim 17, further comprising an expansion chamber, wherein the cooling gas absorbs heat as it changes its phase state while in the expansion chamber.

19. The electrosurgical instrument of claim 18, further comprising an inflow channel and outflow channel for circulating the gas between the fluid pump and the expansion chamber.

20. The electrosurgical instrument of claim 1, wherein the cooling structure comprises a Peltier element.

21. The electrosurgical instrument of any of claims 6 or 11, wherein the surface layer defines an engagement surface for engaging tissue.

22. The electrosurgical instrument of claim 21, wherein the engagement surface is carried on the working end of a probe.

23. The electrosurgical instrument of claim 21, wherein the engagement surface is carried on the working end of a jaw structure, the jaw structure comprising paired first and second jaws moveable between an open position and a closed position.

24. The electrosurgical instrument of claim 23, wherein at least one jaw defines an engagement plane, the engagement plane carrying at least a portion of the engagement surface.

25. The electrosurgical instrument of claim 24, wherein the wherein the cooling structure comprises a thermally conductive material forming an electrode which conducts electrical current from a power source to the PTC matrix.

26. The electrosurgical instrument of claim 25, wherein a plurality of electrodes are formed on the jaw structure, and wherein power is delivered to the electrodes in a bipolar configuration.

27. A method of controlled delivery of energy to tissue, comprising the steps of:
engaging tissue with an engagement surface at least a portion of which comprises a body of temperature-responsive variable impedance material that is intermediate opposing polarity conductor regions operatively coupled to an RF power source;
delivering current flow within the engaged tissue and the engagement surface to cause ohmic heating of the tissue, wherein the ohmically heated tissue conductively heats adjacent regions of the engagement surface, and wherein the engagement surface varies its impedance to modulate current flow between the engagement surface and the tissue; and
contemporaneously cooling the variable impedence body to thereby accelerate modulation of current flow between the engagement surface and the engaged tissue.

28. The method of claim 27, wherein cooling the variable impedance body comprises passively cooling the engagement surface.

29. The method of claim 28, wherein passively cooling the variable impedance body comprises providing a cooling structure at an interior of the working end, wherein the cooling structure comprises a thermally conductive material.

30. The method of claim 28, wherein the cooling structure comprises an electrically conductive material forming an electrode, and wherein delivering current flow comprises delivering RF energy to the engagement surface via the electrically conductive material.

31. The method of claim 27, wherein cooling the variable impedance body comprises actively cooling the engagement surface.

32. The method of claim 31, wherein actively cooling the variable impedance body comprises cooling the engagement surface via a fluid-cooling circulation system.

33. The method of claim 32, wherein cooling the variable impedance body comprises circulating a fluid through a flow channel proximal to the engagement surface.

34. The method of claim 33, wherein cooling the variable impedance body further comprises circulating the fluid through a heat exchanger.

35. The method of claim 33, wherein the fluid comprises water.

36. The method of claim 33, wherein the fluid comprises a cooling gas.

37. The method of claim 36, wherein the cooling gas comprises a cryogen selected from the group consisting of freon or $CO_2$.

38. An electrosurgical instrument for delivering energy to tissue, comprising:

an introducer member having at least one working surface for engaging tissue, wherein at least a portion of the at least one working surface comprises a polymeric PTC composition; and a conductor at an interior of the PTC composition, the conductor having at least one open region at an interior of the conductor for cooling the assembly of the conductor and PTC composition.

39. The electrosurgical instrument of claim 38, wherein the conductor comprises an electrically conductive material forming an electrode, the electrode connected to a radiofrequency power source to ohmically heat the tissue.

40. The electrosurgical instrument of claim 39, wherein the conductive material is also thermally conductive to act as a heat sink.

41. The electrosurgical instrument of claim 38, wherein the open region communicates with a fluid-cooling circulation device.

42. The electrosurgical instrument of claim 41, wherein the fluid cooling circulation device comprises a fluid source for providing fluid flow through the at least one open region.

43. The electrosurgical instrument of claim 42, wherein the fluid source communicates with a heat exchange structure.

44. The electrosurgical instrument of claim 43, wherein the fluid comprises water.

45. The electrosurgical instrument of claim 41, wherein the fluid comprises a cooling gas.

46. The electrosurgical instrument of claim 45, wherein the cooling gas comprises a cryogen selected from the group consisting of freon or $CO_2$.

47. The electrosurgical instrument of claim 40, wherein the working surface defines an engagement surface for engaging tissue.

48. The electrosurgical instrument of claim 47, wherein the engagement surface is carried on the working end of a probe.

49. The electrosurgical instrument of claim 47, wherein the engagement surface is carried on the working end of a jaw structure, the jaw structure comprising paired first and second jaws moveable between an open position and a closed position.

50. The electrosurgical instrument of claim 49, wherein at least one jaw defines an engagement plane, the engagement plane carrying at least a portion of the engagement surface.

* * * * *

UNITED STATES PATENT AND TRADEMARK OFFICE
CERTIFICATE OF CORRECTION

| | | |
|---|---|---|
| PATENT NO. | : 7,169,146 B2 | |
| APPLICATION NO. | : 10/781925 | |
| DATED | : January 30, 2007 | |
| INVENTOR(S) | : Csaba Truckai and John H. Shadduck | |

It is certified that error appears in the above-identified patent and that said Letters Patent is hereby corrected as shown below:

Claim 25, Column 20, Line 8: Delete the words "the wherein".

Signed and Sealed this

Twenty-sixth Day of July, 2011

David J. Kappos
*Director of the United States Patent and Trademark Office*